United States Patent
Shi et al.

(10) Patent No.: US 11,007,141 B2
(45) Date of Patent: *May 18, 2021

(54) ORAL PREPARATION AND PREPARATION METHOD THEREOF

(71) Applicants: GUANGZHOU XIANGXUE PHARMACEUTICAL CO., LTD., Guangzhou (CN); HANGZHOU CONVERD CO., LTD., Hangzhou (CN)

(72) Inventors: Shuiping Shi, Hangzhou (CN); Qingyong Zhang, Hangzhou (CN); Ronghua Zhao, Hangzhou (CN); Huihong Chen, Hangzhou (CN); Lun Zeng, Guangzhou (CN); Daxin Ou, Guangzhou (CN); Yan Liu, Guangzhou (CN)

(73) Assignees: GUANGZHOU XIANGXUE PHARMACEUTICAL CO., LTD., Guangzhou (CN); HANGZHOU CONVERD CO., LTD., Hangzhou (CN)

( * ) Notice: Subject to any disclaimer, the term of this patent is extended or adjusted under 35 U.S.C. 154(b) by 372 days.

This patent is subject to a terminal disclaimer.

(21) Appl. No.: 16/064,466

(22) PCT Filed: Dec. 20, 2016

(86) PCT No.: PCT/CN2016/110973
§ 371 (c)(1),
(2) Date: Aug. 6, 2018

(87) PCT Pub. No.: WO2017/107895
PCT Pub. Date: Jun. 29, 2017

(65) Prior Publication Data
US 2019/0000756 A1   Jan. 3, 2019

(30) Foreign Application Priority Data

Dec. 21, 2015 (CN) .......................... 201510976088.5

(51) Int. Cl.
| | | |
|---|---|---|
| *A61K 9/00* | (2006.01) | |
| *A61K 31/5377* | (2006.01) | |
| *A61K 9/14* | (2006.01) | |
| *A61K 9/20* | (2006.01) | |
| *A61P 35/00* | (2006.01) | |
| *A61K 9/19* | (2006.01) | |
| *A61K 47/69* | (2017.01) | |

(52) U.S. Cl.
CPC ............ *A61K 9/0053* (2013.01); *A61K 9/145* (2013.01); *A61K 9/19* (2013.01); *A61K 9/2018* (2013.01); *A61K 9/2077* (2013.01); *A61K 9/2095* (2013.01); *A61K 31/5377* (2013.01); *A61K 47/6951* (2017.08); *A61P 35/00* (2018.01)

(58) Field of Classification Search
CPC ........................ A61K 31/5377; A61K 47/6951
See application file for complete search history.

(56) References Cited

U.S. PATENT DOCUMENTS

| | | | |
|---|---|---|---|
| 4,727,064 A | * | 2/1988 | Pitha .................... A61K 31/565 |
| | | | 106/205.01 |
| 2005/0215520 A1 | | 9/2005 | Liu et al. |
| 2006/0160800 A1 | | 7/2006 | Hangauer, Jr. |

(Continued)

FOREIGN PATENT DOCUMENTS

| | | |
|---|---|---|
| CN | 101375846 A | 3/2009 |
| CN | 101687798 A | 3/2010 |

(Continued)

OTHER PUBLICATIONS

European Search Report dated Jul. 16, 2019 in the corresponding EP application (application No. 16877705.0).

(Continued)

*Primary Examiner* — James D. Anderson
(74) *Attorney, Agent, or Firm* — Kilpatrick Townsend & Stockton, LLP

(57) ABSTRACT

An oral preparation for treating cell proliferation diseases. The oral preparation comprises hydroxylpropoxyl-β-cyclodextrin and an active component. The active component is KX2-361 or a medicinal salt thereof, and KX2-361 is represented by formula 1. By mixing hydroxylpropoxyl-ydcyclodextrin with KX2-361 or the medicinal salt thereof, an inclusion complex is formed, the solubility of the poorly-soluble drug KX2-361 is greatly improved, and accordingly the drug is prepared into an oral preparation. The oral preparation has good stability, high safety, good absorbability, high bioavailability and economical cost.

21 Claims, 1 Drawing Sheet

(I)

(56) References Cited

U.S. PATENT DOCUMENTS

| | | | |
|---|---|---|---|
| 2008/0221102 A1 | 9/2008 | Hangauer et al. | |
| 2011/0009362 A1* | 1/2011 | Joshi | A61K 47/40 514/58 |
| 2011/0275693 A1 | 11/2011 | Cuypers et al. | |
| 2014/0066445 A1* | 3/2014 | Hangauer, Jr. | A61P 9/00 514/235.5 |
| 2014/0256804 A1* | 9/2014 | Iwata | A61P 17/06 514/456 |
| 2018/0170875 A1 | 6/2018 | Hangauer | |

FOREIGN PATENT DOCUMENTS

| | | |
|---|---|---|
| CN | 102671210 A | 9/2012 |
| CN | 101687798 A | 4/2013 |
| JP | 2005530866 A | 10/2005 |
| JP | 2012082222 A | 4/2012 |
| JP | 2012516303 A | 7/2012 |
| WO | 2006071960 A3 | 5/2007 |
| WO | 2014036426 A1 | 3/2014 |
| WO | 2014082724 A1 | 6/2014 |
| WO | 2014108918 A2 | 7/2014 |

OTHER PUBLICATIONS

JP Office Action dated May 28, 2019 in the corresponding JP application (application No. 2018-533785).

International Search Report and Written Opinion dated Apr. 29, 2015 in the corresponding application (application No. PCT/CN2014/087955).

Loftsson T, Brewster ME, Pharmaceutical applications of cyclodextrins: basic science and product development. J. Pharm. Pharmacol, Nov. 2010;62(11):1607-21.

Wu Peiying, et al., "Progress in solubilization of insoluble drugs, Chinese Traditional Patent Medicine, Sep. 2005, vol. 27, No. 9, p. 1126-1129.".

CN First Office Action with search report dated Sep. 16, 2019 in the corresponding CN application (application No. 201510976088.5).

* cited by examiner

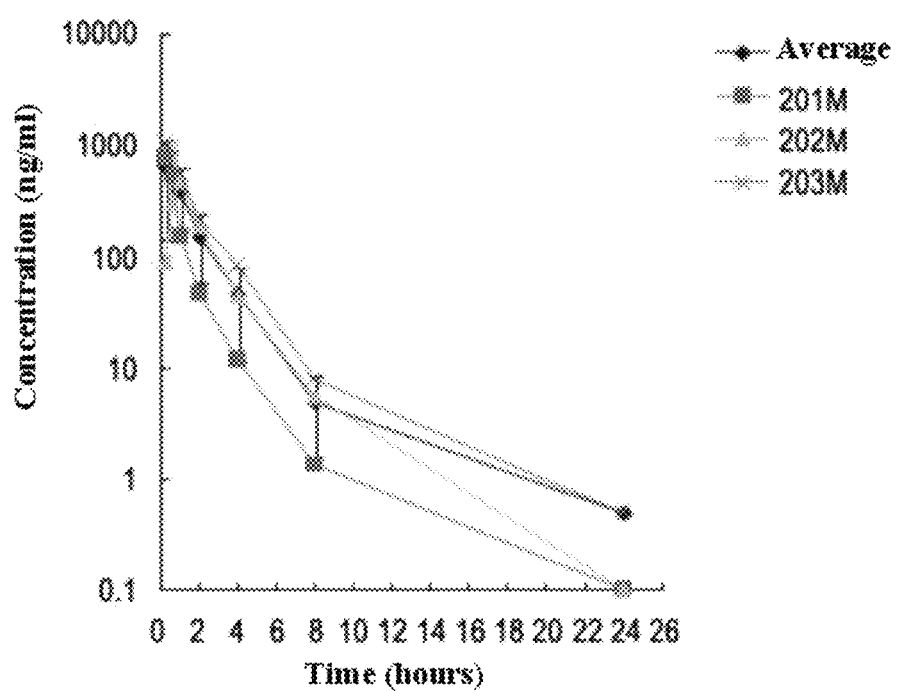

ORAL PREPARATION AND PREPARATION METHOD THEREOF

CROSS-REFERENCE TO RELATED APPLICATIONS

This application is a national stage of International Application No. PCT/CN2016/110973, filed on Dec. 20, 2016, which claims priority to the Chinese Application No. 201510976088.5, filed Dec. 21, 2015, both hereby incorporated by reference in their entireties.

FIELD

The present disclosure belongs to the pharmaceutical field, and specifically relates to an oral preparation and a preparation method thereof.

BACKGROUND

KX2-361 is a small molecule compound developed by Kinex Pharmaceuticals LLC (USA), capable of treating cell proliferative diseases (especially cancer). The compound may treat cell proliferative diseases through tyrosine kinase inhibition (see Patent Document WO2006/071960). KX2-361 has an English chemical name of N-(3-Fluorobenzyl)-2-(5-(4-Morpholinophenyl)pyridin-2-yl)-acetamide), a molecular formula of $C_{24}H_{24}FN_3O_2$, a molecular weight of 405.46 g/mol, and a structural formula as shown in Formula 1:

Fomula 1

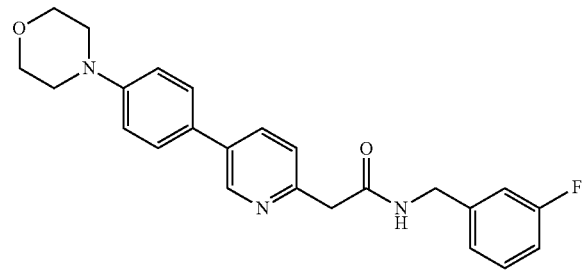

KX2-361 is in the form of free bases and its medicinal salts may be benzene sulfonate, hydrochloride, phosphate and the like. KX2-361 is poorly soluble in water, and its medicinal salts are also undesirable in water solubility and poorly soluble in water. When drug active molecules are poorly soluble in water, oral administration may cause problems such as low bioavailability of the drug and its poor absorbability. When it is to be prepared as a suitable injection, its solubility needs to be increased to meet the needs of intravenous administration. Therefore, for the purpose of KX2-361 or its medicinal salts to be effectively administered to patients, there is an urgent need to find ways to solubilize it.

For poorly soluble drugs, solubilization methods commonly used in the art include: adding surfactant type of solubilizers, adding cosolvents, using mixed solvents, preparing soluble salts, introducing hydrophilic groups into the molecular structure of the main drug, preparing solid dispersions, preparing cyclodextrin inclusion complexes, adding block copolymer solubilizers, preparing liposomes, preparing microemulsions, preparing microspheres and milli microcapsules, adding dendritic macromolecular solubilizers and the like (see Sci-Tech Document: "Wu Peiying, et al., "Progress in solubilization of insoluble drugs", *Chinese Traditional Patent Medicine*, September 2005, Vol. 27, No. 9, p1126-1129.").

It is well known that a variety of cyclodextrins and derivatives thereof can be selected for preparing a drug into a cyclodextrin inclusion complex. Known cyclodextrins include three types, i.e., $\alpha$, $\beta$ and $\gamma$, and each is consisting of 6, 7 and 8 glucoses. It is demonstrated by X-ray diffraction and nuclear magnetic resonance researches that the cyclodextrin has a three-dimensional structure of a circular hollow barrel with wide top and narrow bottom, and opening at both ends, wherein the encapsulated substance molecules enter the barrel to form an inclusion complex. Typically, in the inclusion complex formed by the cyclodextrin and drug, the binding molar ratio of the drug to the cyclodextrin is usually 1:1, but other ratios are also common. Currently, a series of derivatives have been formed on the basis of the above cyclodextrins, and pharmaceutically suitable ones include, for example, methylated-$\beta$-cyclodextrin (RM-($\beta$-CD) and hydroxypropyl-$\beta$-cyclodextrin (HP-$\beta$-CD), sulfobutyl ether-$\beta$-cyclodextrin (SBE-$\beta$-CD), maltose-$\beta$-cyclodextrin, hydroxypropyl-$\gamma$-cyclodextrin (HP-$\gamma$-CD)) and the like. Some worldwide marketed preparations containing cyclodextrins are listed in a Sci-Tech document "Loftsson T, Brewster M E. Pharmaceutical applications of cyclodextrins: basic science and product development. *J. Pharm. Pharmacol.* 2010 November; 62(11):1607-21.", for example, alprostadil injection and cefotiam hydrochloride tablets each containing $\alpha$-cyclodextrin; cephalosporin tablets and benexate hydrochloride capsules each containing $\beta$-cyclodextrin; Tc-99m injection containing $\gamma$-cyclodextrin; voriconazole injection and ziprasidone mesylate injection each containing SBE-$\beta$-CD; and, itraconazole oral solution and injection, and mitomycin injection each containing HP-$\beta$-CD. However, different cyclodextrins and their derivatives are suitable for different drugs, and at present, based on the specific structure of a given compound, it is difficult to speculate which cyclodextrin or its derivative is suitable in solubilizing ability.

The aforementioned patent document WO2006/071960 discloses a compound with a general formula including a series of specific compounds such as KX2-361 and the like, which can be administered in various ways such as oral administration, injection administration, rectal administration, pulmonary administration, intranasal administration, transient administration, fluctuating release administration, and the like. The patent document further discloses that different forms of solid dosage forms, liquid dosage forms and the like can be used for different administration methods. The patent document also discloses that injectable liquid medicines can be prepared using solvents which include, for example, sesame or peanut oil, and aqueous propylene glycol; or, injectable liquid medicines can be prepared using aqueous solutions of water soluble medicinal salts of KX2-361, in specific examples, the dispersible phases may be glycerol, liquid polyethylene glycol and mixtures thereof in oil. The patent document also discloses dosage forms (such as liquid dosage forms) comprising cyclic or aliphatic encapsulants or dissolvents, and the cyclic or aliphatic encapsulants or dissolvents are, for example, cyclodextrin, polyether and polysaccharide; specifically preferred examples include methyl cellulose or CAPTISOL® (i.e., sulfobutyl ether-$\beta$-cyclodextrin). That is, this patent document discloses some solubilization methods and solubilizing reagents that are generally used in the art for poorly soluble drugs. However, the inventors of the present disclosure have found that the specific solubilization methods and solubilizing reagents disclosed in document WO 2006/071960 are not desirable in the development of KX2-361 drugs and are not suitable for further development of KX2-361 as a cost effective drug preparation that can be effectively administered to patients. Therefore, there is still an urgent need to find more pharmaceutically suitable solubilization methods and solubilizing reagents for KX2-361 or medicinal salts thereof.

SUMMARY OF THE DISCLOSURE

In order to solve the problems existing in the above prior art, the present disclosure provides an oral preparation and a preparation method thereof.

Specifically, the present disclosure provides:

(1) An oral preparation for treatment of cell proliferative diseases, comprising hydroxypropyl-β-cyclodextrin and an active ingredient that is KX2-361 or a medicinal salt thereof, KX2-361 is represented by the following formula 1:

Fomula1

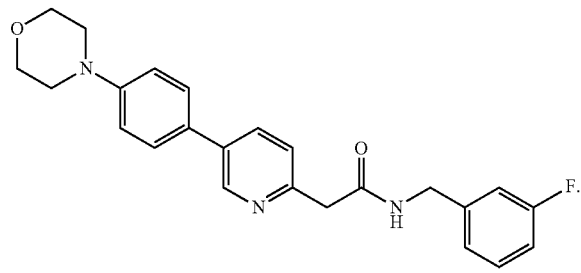

(2) The oral preparation of (1), wherein the molar ratio of the active ingredient to hydroxypropyl-β-cyclodextrin is 1:(4-59).

(3) The oral preparation of (1), wherein the active ingredient is KX2-361, KX2-361.monophenyl sulfonate, KX2-361.dihydrochloride, KX2-361.monophosphate and/or KX2-361.diphosphonate.

(4) The oral preparation of (1), wherein at least part of the active ingredient is encapsulated by at least a part of the hydroxypropyl-β-cyclodextrin to form a drug inclusion complex.

(5) The oral preparation of (1), further comprising a medicinal excipient.

(6) The oral preparation of (5), wherein the medicinal excipient is one or more selected from the group consisting of a filler, a disintegrant and a lubricant.

(7) The oral preparation of (6), wherein the filler is one or more selected from the group consisting of a microcrystalline cellulose, a lactose, a starch and a mannitol, and the amount of the filler is 0%~69% (w/w) based on the total weight of the oral preparation.

(8) The oral preparation of (6), wherein the disintegrant is one or more selected from the group consisting of croscarmellose sodium, cross-linked povidone and sodium carboxymethyl starch, and the content of the disintegrant is 0%~5% (w/w) based on the total weight of the oral preparation.

(9) The oral preparation of (6), wherein the lubricant is one or more selected from the group consisting of magnesium stearate, micro powder silica gel and talcum powder, and the content of the lubricant is 0.5% (w/w)~3% (w/w) based on the total weight of the oral preparation.

(10) The oral preparation of (1), wherein the oral preparation is in the form of a tablet, wherein the content of the active ingredient in a single dose of tablet is 0.5% (w/w)~6.5% (w/w).

(11) A method of preparing the oral preparation of any one of (1) to (10), comprising the following steps:

A) providing a first solution in which hydroxypropyl-β-cyclodextrin is dissolved, the first solution has a pH value of 1~2;

B) mixing KX2-361 or a medicinal salt thereof with the first solution to prepare a second solution in which the KX2-361 or the medicinal salt thereof is dissolved.

C) drying the second solution to obtain a dried product.

(12) The method of (11), wherein in the first solution, the hydroxypropyl-β-cyclodextrin has a concentration of 10% (w/v)~50% (w/v).

(13) The method of (11), wherein in the second solution, the KX2-361 or the medicinal salt thereof has a concentration of 0.5 mg/ml to 15 mg/ml, preferably of 0.5 mg/ml to 10 mg/ml, measured by KX2-361.

(14) The method of (11), wherein in the second solution, a molar ratio of the KX2-361 or the medicinal salt thereof to the hydroxypropyl-β-cyclodextrin is 1:(4~59).

(15) The method of (11), further comprising I) adjusting the pH value of the second solution to 3~before the step C) and after the step B).

(16) The method of (11), further comprising D) tableting the dried product after the step C).

(17) The method of (16), wherein the step D) includes mixing the dried product with one or more excipients selected from the group consisting of filler, disintegrant and lubricant, then performing the tableting.

(18) The method of (17), wherein the filler is one or more selected from the group consisting of a microcrystalline cellulose, a lactose, a starch and a mannitol, and the content of the filler is 0%~69% (w/w) based on the total weight of the oral preparation.

(19) The method of (17), wherein the disintegrant is one or more selected from the group consisting of croscarmellose sodium, cross-linked povidone (PVPP) and sodium carboxymethyl starch, and the content of the disintegrant is 0%~5% (w/w) based on the total weight of the oral preparation.

(20) The method of (17), wherein the lubricant is one or more selected from the group consisting of a magnesium stearate, a micro powder silica gel and a talcum powder, and the content of the lubricant is 0.5%~3% (w/w) based on the total weight of the oral preparation.

(21) The method of (11), wherein the medicinal salt of KX2-361 is KX2-361.monophenyl sulfonate, KX2-361.dihydrochloride, KX2-361.monophosphate and/or KX2-361.diphosphonate.

The present disclosure has the following advantages and positive effects compared with the prior art:

1. In the present disclosure, by mixing hydroxypropyl-β-cyclodextrin with KX2-361 or its medicinal salt to form an inclusion complex, the solubility of the poorly soluble drug KX2-361 is greatly improved, and hydroxypropyl-β-cyclodextrin shows higher solubilizing ability compared with other cyclodextrins and derivative adjuvants thereof, injectable surfactant solutions, injectable menstruums or composite menstruums.

2. In the present disclosure, by mixing hydroxypropyl-β-cyclodextrin with KX2-361 or its medicinal salt to form an inclusion complex, the poorly soluble KX2-361 or its medicinal salt can be formulated into a stable liquid preparation from which a lyophilized preparation can then be prepared, and thereby, a variety of drug preparations that can be clinically administrated to patients can be prepared, including: intravenous preparations (e.g., intravenous injections or intravenous drips), oral preparations (such as tablets) and the like.

3. The present disclosure further optimizes the inclusion process and optimizes the drug-loading formulation for intravenous preparations and oral preparations to obtain drug preparations that can be directly intravenously injected and intravenous drip preparations that can be diluted within 10 times, as well as oral preparations, and each indicator of the above preparations (including drug redissolution, placement stability and dissolution) are qualified, and to achieve the maximum optimization of drug loading. These drug preparations have good stability, high safety, good absorbability, high bioavailability and relatively low cost.

BRIEF DESCRIPTION OF DRAWINGS

FIG. 1 is a graph showing a plasma concentration as a function of time, after oral administration of a tablet of prescription B4 according to Example 7 of the present disclosure. Wherein, the horizontal axis represents time in unit of hour and the vertical axis represents the plasma concentration of KX2-361 in unit of ng/ml after oral administration to male beagle dogs at a dose of 51 mg/dog (measured by KX2-361).

DETAILED DESCRIPTION OF EMBODIMENTS

The present disclosure will be further described below through the description of specific embodiments with reference to the accompanying drawings, but without limiting the present disclosure, and those skilled in the art can make various modifications or improvements according to the basic idea of the present disclosure, which are within the scope of the present disclosure as long as they do not depart from the basic idea of the present disclosure.

As used herein, the term "injection" refers to a sterile solution (including true solution, emulsion, and suspension) prepared from a drug to be injected into body, and a lyophilized powder or concentrated solution to be formulated into the sterile solution (including true solution, emulsion, and suspension) before use.

As used herein, the term "intravenous drip" refers to a method of infusing, by an infusion tube, a large amount of liquid containing drugs into body through vein. Intravenous drip is also known as "infusion", "drip", "intravenous drip" and "hanging water".

As used herein, the term "intravenous preparation" is intended to encompass "intravenous injection" and "intravenous drip", and include "lyophilized powder" that can be used to formulate intravenous injection solution and intravenous drip solution.

As used herein, the term "oral preparation" refers to a preparation form administered orally and drugs therein being absorbed into the blood in the gastrointestinal tract, wherein the oral preparation includes tablet, granule, capsule, oral solution, and the like.

As used herein, the term "cell proliferative diseases" includes the diseases described in patent document WO2006/071960, which refers to a state of uncontrolled proliferation and/or abnormal growth for cell, and includes cancers or non-cancerous diseases. "Cancers" include solid tumors such as lung cancer, breast cancer, colon cancer, ovarian cancer, brain cancer, liver cancer, pancreatic cancer, prostate cancer, malignant melanoma, non-melanoma skin cancer, and malignant blood tumor such as childhood leukemias and lymphomas, multiple myeloma, Hodgkin's diseases, lymphomas of lymphocytes and primary skin, as well as acute and chronic leukemias such as acute lymphoblastic, acute myeloid or chronic myeloid leukemia, plasma cell neoplasms, lymphoid neoplasms and AIDS-related cancers. Non-cancerous diseases include, for example, psoriasis, epithelial and dermoid cysts, lipomas, adenomas, hairy and cutaneous hemangiomas, lymphangiomas, spider angioma lesions, teratomas, nephromas, myofibromas, osteoplastic tumors, other dysplastic aggregations and other similar diseases.

As used herein, the term "inclusion complex" refers to a unique form of complex formed by a drug molecule structure being completely or partially encapsulated into the molecular cavity of another substance. Inclusion complexes are active in the research field of drug preparation. In the 1950s, researchers have recognized that inclusion complexes have an impact on the properties of drugs, for example, the inclusion complexes increase the solubility and stability of drugs, and affect the absorption, distribution and onset time of drugs in body.

As used herein, the term "active ingredient" refers to drug molecules that has therapeutic effects on cell proliferative diseases, for example, KX2-361 or medicinal salt thereof as described herein.

The medicinal salts of KX2-361 described herein include, for example, benzene sulfonate of KX2-361, hydrochloride of KX2-361, phosphate of KX2-361, and the like. The medicinal salts of KX2-361 described herein may be mono-salt or di-salt forms of KX2-361, including, for example, KX2-361.monophenyl sulfonate, KX2-361.dihydrochloride, KX2-361.monophosphate and/or KX2-361.diphosphate.

As used herein, the term "inclusion ingredient" refers to a substance that encapsulates all or part of a drug molecule structure into its molecular cavity, such as hydroxypropyl-β-cyclodextrin described herein.

As used herein, the term "hydroxypropyl-β-cyclodextrin" refers to the etherate of beta-cyclodextrin and 1,2-oxirane; the content of hydroxypropoxy ($-OCH_2CHOHCH_3$) measured by anhydrate is 19.6%-26.3% (see the *Chinese Pharmacopoeia Part IV*, 2015 Edition).

I. Pharmaceutical Composition

Since KX2-361 and its medicinal salts have properties of poor water-solubility, the inventors of the present disclosure hope to find a method of effectively solubilizing the same so as to formulate them into clinically applicable drug preparations. As described above, various methods for solubilizing a drug are known, and various solubilization methods are listed in patent document WO2006/071960 specifically for KX2-361 or a medicinal salt thereof. However, the inventors of the present disclosure found that these solubilization methods for KX2-361 or a medicinal salt thereof are undesirable. At present, it is difficult to speculate on which solubilization method or solubilizing reagent has most suitable ability for solubilizing a given compound according to the specific structure of the compound. Therefore, for the KX2-361 and its medicinal salts, the inventors of the present disclosure conducted a large number of researching and screening work on different solubilization methods and different solubilizing reagents, they finally found that KX2-361 or a medicinal salt thereof can be effectively solubilized by using inclusion technology, and surprisingly found that the most suitable inclusion agent is hydroxypropyl-β-cyclodextrin.

Accordingly, the present disclosure provides a pharmaceutical composition including hydroxypropyl-β-cyclodextrin and an active ingredient that is KX2-361 or a medicinal salt thereof, the KX2-361 is represented by the following formula 1:

Fomula1

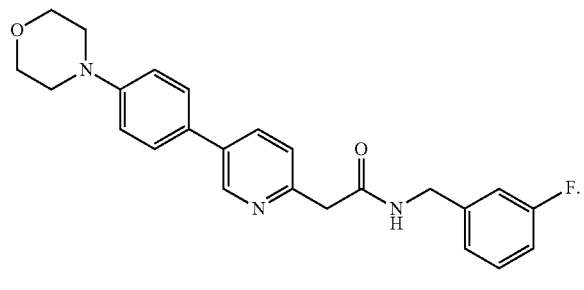

Preferably, the molar ratio of the active ingredient to hydroxypropyl-β-cyclodextrin in the pharmaceutical composition is 1:(1-250), preferably 1:(4-59), for example, 1:(9-59), or for example, 1:(4-17).

Preferably, the mass ratio of KX2-361 contained in the active ingredient to hydroxypropyl-β-cyclodextrin in the pharmaceutical composition is (0.1-29):100, more preferably (0.5-5):100, for example, (2-2.5):100, (0.5-1.5):100, or (0.5-0.7):100, etc.

Preferably, the active ingredient is KX2-361, KX2-361.monophenyl sulfonate, KX2-361.dihydrochloride, KX2-361.monophosphate and/or KX2-361.diphosphonate, wherein preferably is KX2-361.monophenyl sulfonate. As used herein, unless otherwise specified, the "KX2-361.benzene sulfonate" refers to KX2-361.monophenyl sulfonate, which has a molecular weight of 563.64.

In the pharmaceutical composition of the present disclosure, at least a portion of the active ingredient may be encapsulated by at least a portion of the hydroxypropyl-β-cyclodextrin to form a drug inclusion complex. In the drug inclusion complex, the hydroxypropyl-β-cyclodextrin can form a hollow barrel structure with openings at both ends, and the KX2-361 or a medicinal salt thereof can be completely or partially encapsulated in the barrel structure.

Preferably, the pharmaceutical composition of the present disclosure further includes a medicinal excipient.

The excipient can be selected according to a required dosage form. For example, when the dosage form is an intravenous preparation, the excipient may be one or more selected from the group consisting of a mannitol, a lactose, a dextran, a xylitol, a sorbitol, a glucose, and a sodium chloride. In addition, when the dosage form is an oral preparation, the excipient also may be one or more selected from the group consisting of a filler, a disintegrant and a lubricant. The filler may be one or more selected from the group consisting of a microcrystalline cellulose, a lactose, a starch, a mannitol and the like, the disintegrant may be one or more selected from the group consisting of croscarmellose sodium, cross-linked povidone, carboxymethyl starch sodium and the like, and the lubricant may be one or more selected from the group consisting of magnesium stearate, micro powder silica gel and talcum powder and the like.

The present disclosure also provides a use of the pharmaceutical composition in the preparation of a drug for treatment of cell proliferative diseases.

II. Pharmaceutical Inclusion Complex

In another aspect, the present disclosure also provides a drug inclusion complex including an active ingredient and an inclusion ingredient encapsulating the active ingredient, wherein the inclusion ingredient is hydroxypropyl-β-cyclodextrin, and the active ingredient is KX2-361 or a medicinal salt thereof, the KX2-361 is represented by the following formula 1:

Fomula1

In the drug inclusion complex, the hydroxypropyl-β-cyclodextrin can form a hollow barrel structure with openings at both ends, and the KX2-361 or the medicinal salt thereof can be completely or partially encapsulated in the barrel structure.

Preferably, the active ingredient is KX2-361, KX2-361.monophenyl sulfonate, KX2-361.dihydrochloride, KX2-361.monophosphate and/or KX2-361.diphosphonate, wherein it preferably is KX2-361.monophenyl sulfonate. As used herein, unless otherwise specified, the "KX2-361.benzene sulfonate" refers to KX2-361.monophenyl sulfonate, which has a molecular weight of 563.64.

III. Intravenous Preparation

In another aspect, the present disclosure also provides an intravenous preparation for treatment of cell proliferative diseases, wherein the preparation includes the pharmaceutical composition of the present disclosure.

Preferably, in the intravenous preparation, the molar ratio of the active ingredient to hydroxypropyl-β-cyclodextrin is 1:(1-250), more preferably 1:(9-59), for example, 1:(9-15), 1:(12-59), 1:(16-53), 1:(31-56), etc.

Preferably, in the intravenous preparation, the mass ratio of KX2-361 contained in the active ingredient to hydroxypropyl-β-cyclodextrin is (0.1-29):100, more preferably (0.5-2.5):100, for example, (2-2.5): 100, (0.5-2):100, (0.5-1.5): 100, or (0.5-0.7): 100, etc.

The intravenous preparation of the present disclosure may comprise an excipient which is preferably one or more selected from the group consisting of a mannitol, a lactose, a dextran, a xylitol, a sorbitol, a glucose and a sodium chloride.

The intravenous preparation may be in the form of lyophilized powder or it also may be in the form of a liquid preparation. When the intravenous preparation is a liquid preparation, the concentration of hydroxypropyl-β-cyclodextrin in the liquid preparation may be 100 mg/ml to 500 mg/ml, preferably 200 mg/ml to 400 mg/ml; the concentration of the KX2-361 or the medicinal salt thereof measured by KX2-361 may be 0.5 mg/ml to 5 mg/ml, preferably 1.4 mg/m to 4.3 mg/ml.

The lyophilized powder may be redissolved with a solution for injection to prepare a liquid preparation. Any solution for injection known in the art may be used as the solution for injection, for example, the solution for injection may be buffered saline solution, glucose aqueous solution, sodium chloride aqueous solution or lactated Ringer's solution. The buffered saline solution, for example, may be citrate buffer solution, acetic acid-sodium acetate buffer solution, phosphate buffer solution and the like; the glucose aqueous solution, for example, may be 5% (w/v) glucose aqueous solution; and the sodium chloride aqueous solution, for example, may be 0.9%(w/v) sodium chloride aqueous solution. Preferably, the buffered saline solution is a buffered saline solution with a pH value of 4.0, such as a citrate buffer solution with a pH value of 4.0.

In another aspect, the present disclosure also provides a method of preparing the intravenous preparation of the present disclosure, including the following steps:

1) Providing a first solution in which hydroxypropyl-β-cyclodextrin is dissolved, the first solution being an aqueous solution with a pH value of 1 to 2;

2) Mixing KX2-361 or a medicinal salt thereof with the first solution to prepare a second solution in which KX2-361 or the medicinal salt thereof is dissolved.

Preferably, the concentration of hydroxypropyl-β-cyclodextrin in the first solution is 10% (w/v) to 50% (w/v), more preferably 20% (w/v) to 40% (w/v), further preferably 30% (w/v) to 40% (w/v). If the concentration of hydroxypropyl-β-cyclodextrin is less than 10% (w/v), the amount of inclusion drug is too low; while if the concentration of hydroxypropyl-β-cyclodextrin is more than 50% (w/v), then the formulated solution will have a viscosity that is too high to be freeze-dried. The first solution may contain a pH adjuster which may be a strong acidic solution such as hydrochloric acid and the like.

Preferably, the concentration of KX2-361 or the medicinal salt thereof in the second solution measured by KX2-361 is 0.5 mg/ml to 5 mg/ml, preferably 1.4 mg/ml to 4.3 mg/ml. If the concentration of KX2-361 is less than 0.5 mg/ml, the amount of inclusion drug is too low; while if the concentration of KX2-361 is more than 5 mg/ml, then after redissolving the formulated lyophilized powder, the obtained redissolved solution and the solution formed with other dilution media will have poor stability, and the drug is easy to precipitate. The medicinal salt of the KX2-361 may be KX2-361.monophenyl sulfonate, KX2-361.dihydrochloride, KX2-361.monophosphate and/or KX2-361.diphosphonate, wherein preferably KX2-361.monophenyl sulfonate.

Preferably, in the second solution, the molar ratio of KX2-361 or the medicinal salt thereof to hydroxypropyl-β-cyclodextrin is 1:(1-250), more preferably 1:(9-59).

Regarding to the pH value of the first solution, since KX2-361 or the medicinal salt thereof is not stable to acid, if the pH value of the first solution is lower than 1, it will cause a significant increase in acid degradation impurities; if the pH value of the first solution is higher than 2, the drug will have a slow dissolution rate and a significantly increased dissolution time, on the one hand, leading to great inconvenience for production, and on the other hand, increasing the amount of acid degradation impurities. More preferably, the pH value of the first solution is 1.2-2.0.

In the step 2) of the method of the present disclosure, the drug inclusion complex of the present disclosure is obtained.

In the step 2) of the method of the present disclosure, the mixing includes mixing by stirring or by ultrasound.

Still preferably, the method of the present disclosure further includes step 3): freeze-drying the second solution to prepare a lyophilized powder. The freeze-drying can be performed using conventional methods in the art.

Still preferably, before the step 3) and after the step 2), the method further includes a step i): adjusting the pH value of the second solution to 3-7, more preferably to 4-6. This step of adjusting pH value is beneficial to prevent drug from degradation due to the long time of follow-up freeze-drying process and acid residues in the lyophilized sample. Optional pH adjusters include alkaline solutions such as NaOH aqueous solution and the like. In this step of adjusting the pH value, if the pH value is adjusted to more than 7, the hydroxypropyl-β-cyclodextrin will have poor encapsulating effect on KX2-361 or the medicinal salt thereof, thereby, KX2-361 or the medicinal salt thereof is easy to precipitate. In this step of adjusting the pH value, if the pH value is adjusted to less than 3, since the KX2-361 structure is easy to degrade in acid due to ring openning, degradation impurities will be increased significantly and the resulting preparation will be unstable.

Still preferably, before the step 3) and after the step 2), the method further includes a step ii): sterile filtering (the second solution). Processes of sterile filtering are well known in the art, for example, a filter membrane may be used for filtering, for example, a 0.22 μm filter membrane is used to physically trap live microorganisms.

The solution obtained after sterile filtering may be directly filled into a small-volume injection, or may be freeze-dried to obtain a lyophilized powder. The lyophilized powder may be redissolved to obtain an injection for injection administration, or the lyophilized powder may be diluted with a large-volume diluent to obtain a drip solution for drip administration.

Still preferably, before step ii) and after step i), the method further includes a step of removing pyrogen. Processes for removing pyrogen are well known in the art, for example, adding activated carbon to remove pyrogen and then filtering off the activated carbon.

In a specific embodiment of the present disclosure, the method of preparing the intravenous preparation of the present disclosure includes the following sequential steps:

a) Preparing a hydrochloric acid solution with a pH value of 1.2-2.0 using an appropriate amount of concentrated hydrochloric acid and water for injection;

b) Adding a prescribed amount of hydroxypropyl-β-cyclodextrin to the hydrochloric acid solution obtained in the step a) and stirring to dissolve; then adding a prescribed amount of KX2-361 or a medicinal salt thereof, and stirring or using ultrasound to dissolve;

c) Adjusting the pH value of the solution obtained in the step b) to 4.0-6.0 with sodium hydroxide aqueous solution;

d) Removing pyrogen by adding activated carbon for absorption and filtering off the activated carbon;

e) Sterile filtering;

f) Freeze-drying.

As a preferred embodiment of the present disclosure, the freeze-drying process in the above step f) is carried out under conditions that vacuum degree and temperature are controlled, and the temperature control process may be, for example, thermal insulating for 2-5 hours at −40° C. to −50° C.; warming up to −20° C. over 5-7 hours, and thermal insulating for 5-7 hours; warming up to 0° C. over 5-7 hours, and thermal insulating for 5-7 hours; warming up to 10° C. over 5-7 hours, and thermal insulating for 5-8 hours until the sample is dry.

In another preferred embodiment of the present disclosure, when the concentration of hydroxypropyl-β-cyclodextrin is 10% (w/v), the molar ratio of KX2-361 or its medicinal salt to hydroxypropyl-β-cyclodextrin is 1:(31-56); when the concentration of hydroxypropyl-β-cyclodextrin is 20% (w/v), the molar ratio of KX2-361 or its medicinal salt to hydroxypropyl-β-cyclodextrin is 1:(16-53); when the concentration of hydroxypropyl-β-cyclodextrin is 30% (w/v), the molar ratio of KX2-361 or its medicinal salt to hydroxypropyl-β-cyclodextrin is 1:(12-59); and when the concentration of hydroxypropyl-β-cyclodextrin is 40% (w/v), the molar ratio of KX2-361 or its medicinal salt to hydroxypropyl-β-cyclodextrin is 1:(9-15).

In the preparation of a liquid preparation of the intravenous preparation, the method further comprises the step of redissolving the lyophilized powder with a solution for injection. Any solution for injection known in the art may be used, for example, buffered saline solution, glucose aqueous solution, sodium chloride aqueous solution or lactated Ringer's solution. The buffered saline solution, for example, may be citrate buffer solution, acetic acid-sodium acetate buffer solution, phosphate buffer solution and the like; the glucose aqueous solution, for example, may be 5% (w/v) glucose aqueous solution; and the sodium chloride aqueous solution, for example, may be 0.9% (w/v) sodium chloride aqueous solution. Preferably, the buffered saline solution is a buffered saline solution with a pH value of 4.0, such as a citrate buffer solution with a pH value of 4.0.

In the present disclosure, in the study of intravenous preparation, the inclusion process is optimized so as to optimize the drug-loading formulation, finally, to obtain the formulations that can be directly administered intravenously and intravenous drip formulations that can be diluted within 10 times, and all indicators of the above formulations are qualified. After the administration of intravenous injection or intravenous drip, the behavior of the drug in blood vessels can be detected by dynamic and static simulation tests, and the inventors have found that no precipitation phenomenon is present. Therefore, the present disclosure provides a preparation formulation that can be safely administered by injection. The present disclosure also conducts preliminary stability tests on the lyophilized powder, and the test results show that the preparation is stable after being left for 3 months under conditions of 40° C., 25° C.

IV. Oral Preparation

In another aspect, the present disclosure also provides an oral preparation for treatment of cell proliferative diseases, including hydroxypropyl-β-cyclodextrin and an active ingredient that is KX2-361 or a medicinal salt thereof, and the KX2-361 is represented by the following formula 1:

Fomula1

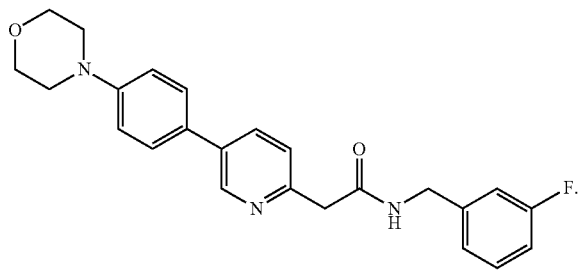

Preferably, in the oral preparation, the molar ratio of the active ingredient to hydroxypropyl-β-cyclodextrin is 1:(1-250), more preferably 1:(4-59), further preferably 1:(4-17).

Still preferably, in the oral preparation, the mass ratio of KX2-361 contained in the active ingredient to hydroxypropyl-β-cyclodextrin measured by KX2-361 is (0.1-29):100, more preferably (0.5-5):100, further preferably (1.7-5):100.

Preferably, the active ingredient is KX2-361, KX2-361.monophenyl sulfonate, KX2-361.dihydrochloride, KX2-361.monophosphate and/or KX2-361.diphosphonate, wherein preferably KX2-361.monophenyl sulfonate. As used herein, unless otherwise specified, the "KX2-361.benzene sulfonate" refers to KX2-361.monophenyl sulfonate, which has a molecular weight of 563.64.

In the oral preparation of the present disclosure, at least a portion of the active ingredient can be encapsulated by at least a portion of the hydroxypropyl-β-cyclodextrin to form a drug inclusion complex. In the drug inclusion complex, the hydroxypropyl-β-cyclodextrin can form a hollow barrel structure with openings at both ends, and the KX2-361 or the medicinal salt thereof can be completely or partially encapsulated in the barrel structure.

Preferably, the oral preparation of the present disclosure further includes a medicinal excipient. The medicinal excipient may be one or more selected from the group consisting of a filler, a disintegrant and a lubricant.

The filler may be one or more selected from the group consisting of a microcrystalline cellulose (MCC), a lactose, a starch, a mannitol and the like, wherein the lactose is preferred; the content of the filler is preferably 0%-69% (w/w) based on the total weight of the oral preparation. The disintegrant may be one or more selected from the group consisting of croscarmellose sodium (CC-Na), cross-linked povidone (PVPP), sodium carboxymethyl starch and the like, wherein the croscarmellose sodium is preferred; the content of the disintegrant is preferably 0%-5% (w/w) based on the total weight of the oral preparation. The lubricant may be one or more selected from the group consisting of magnesium stearate, micro powder silica gel, talcum powder and the like, wherein magnesium stearate is preferred; the content of the lubricant is 0.5%-3% (w/w) based on the total weight of the oral preparation.

Preferably, the oral preparation is in the form of tablet, wherein the content of the active ingredient in a single tablet is 0.5%-6.5% (w/w).

In a specific embodiment of the present disclosure, the tablet of the present disclosure contains: about 1% (w/w) of KX2-361.monophenylsulfonate, more than 28.6% (w/w) and less than 29% (w/w) of hydroxypropyl-β-cyclodextrin, about 64% (w/w) of lactose, about 5% (w/w) of croscarmellose sodium, about 1% (w/w) of magnesium stearate, and more than 0 and less than 0.4% (w/w) of NaCl.

In another aspect, the present disclosure also provides a method of preparing the oral preparation of the present disclosure, comprising the following steps:

A) Providing a first solution in which hydroxypropyl-β-cyclodextrin is dissolved, the first solution being with a pH value of 1-2;

B) Mixing KX2-361 or its medicinal salt with the first solution to prepare a second solution in which KX2-361 or its medicinal salt is dissolved.

C) Drying the second solution to obtain a dried product.

Preferably, the concentration of hydroxypropyl-β-cyclodextrin in the first solution is 10% (w/v) to 50% (w/v), more preferably 20% (w/v) to 40% (w/v), further preferably 30% (w/v) to 40% (w/v). If the concentration of hydroxypropyl-β-cyclodextrin is less than 10% (w/v), the amount of inclusion drug is too low; if it is more than 50% (w/v), the formulated solution has a viscosity that is too high to be dried (for example, freeze-dried). The first solution may contain a pH adjuster which may be a strong acidic solution such as hydrochloric acid.

Preferably, in the second solution, the concentration of KX2-361 or a medicinal salt thereof measured by KX2-361 is 0.5 mg/ml to 15 mg/ml, preferably 3.6 mg/ml to 15 mg/kg, more preferably 5 mg/ml to 10 mg/ml. If the concentration of KX2-361 is lower than 0.5 mg/ml, the amount of the inclusion drug is too low; if it is more than 15 mg/ml, the stability of the inclusion system is poor and the drug is easy to precipitate. The medicinal salt of the KX2-361 may be KX2-361.monophenyl sulfonate, KX2-361.dihydrochloride, KX2-361.monophosphate and/or KX2-361.diphosphonate, wherein KX2-361.monophenyl sulfonate is preferred.

Preferably, in the second solution, the molar ratio of KX2-361 or a medicinal salt thereof to hydroxypropyl-β-cyclodextrin is 1:(1-250), more preferably 1:(4-59), further preferably 1:(4-17).

In regard to the pH value of the first solution, since KX2-361 or medicinal salt thereof is not stable to acid, then if the pH of the first solution is lower than 1, it will cause a significant increase in acid degradation impurities; if the pH of the first solution is higher than 2, the drug will have a slow dissolution rate and a significantly increased dissolution time, on the one hand, this will lead to great inconvenience for production, and on the other hand, also increase the amount of acid degradation impurities. More preferably, the pH value of the first solution is 1.2-2.0.

In the step B) of the method of the present disclosure, the mixing includes mixing by stirring or by ultrasound.

In the step C) of the method of the present disclosure, examples of drying include freeze-drying, spray drying and the like. Freeze-drying and spray-drying can be performed using conventional methods in the art.

Still preferably, before the step C) and after the step B), the method further comprises a step I): adjusting the pH value of the second solution to 3-7, more preferably to 4-6. This step of adjusting the pH value is beneficial to prevent drug from degradation due to the long time of follow-up freeze-drying process and acid residues in the lyophilized sample. Optional pH adjusters include alkaline solutions such as NaOH aqueous solution and the like. In this step of adjusting the pH value, if the pH value is adjusted to more than 7, the hydroxypropyl-β-cyclodextrin will have poor encapsulating effect on KX2-361 or a medicinal salt thereof, thereby, KX2-361 or a medicinal salt thereof is easy to precipitate. If the pH value is adjusted to less than 3, since the KX2-361 structure is easy to degrade in acid due to ring opening, the degradation impurities will increase significantly and the resulting preparation will be unstable.

Still preferably, before the step C) and after the step B), the method further includes a step III): filtering. Processes of filtering are well known in the art, for example, filtering with a filter membrane such as a 0.8 μm filter membrane to obtain a clear solution.

Preferably, after the step C), the method further includes a step D): tableting the dried product. Specifically, the step D) includes mixing the dried product with an excipient which is one or more selected from the group consisting of a filler, a disintegrant and a lubricant, and then performing the tableting.

The filler may be one or more selected from the group consisting of a microcrystalline cellulose (MCC), a lactose, a starch, a mannitol and the like, wherein the lactose is preferred; the content of the filler is preferably 0%-69% (w/w) based on the total weight of the oral preparation. The disintegrant may be one or more selected from the group consisting of croscarmellose sodium (CC-Na), cross-linked povidone (PVPP), sodium carboxymethyl starch and the like, wherein the croscarmellose sodium is preferred; the content of the disintegrant is preferably 0%-5% (w/w) based on the total weight of the oral preparation. The lubricant may be one or more selected from the group consisting of magnesium stearate, micro powder silica gel, talcum powder and the like, wherein the magnesium stearate is preferred; the content of the lubricant is 0.5%-3% (w/w) based on the total weight of the oral preparation.

In a specific embodiment of the present disclosure, the method of preparing the oral preparation according to the present disclosure includes the following sequential steps:

① Preparing a hydrochloric acid solution with a pH value of 1.2-2.0 using an appropriate amount of concentrated hydrochloric acid and water for injection;

② Adding a prescribed amount of hydroxypropyl-β-cyclodextrin to the hydrochloric acid solution obtained in step ① and stirring to dissolve; then adding a prescribed amount of KX2-361 or a medicinal salt thereof, and stirring or using ultrasound to dissolve;

③ Adjusting the pH value of the solution obtained in step to 4.0-6.0 with sodium hydroxide aqueous solution;

④ Filtering;

⑤ Freeze-drying;

⑥ Sieving the lyophilized powder obtained in step ⑤;

⑦ Mixing the sieved substance obtained in step ⑥ with an excipient which is one or more selected from the group consisting of a filler, a disintegrant and a lubricant;

⑧ Tableting.

As a preferred embodiment of the present disclosure, the freeze-drying process in the above step ⑤ is carried out under conditions that vacuum degree and temperature are controlled, and the temperature control process may be, for example, thermal insulating for 2-5 hours at −40° C. to −50° C.; warming up to −20° C. over 5-7 hours, and thermal insulating for 5-7 hours; warming up to 0° C. over 5-7 hours, and thermal insulating for 5-7 hours; warming up to 10° C. over 5-7 hours, and thermal insulating for 5-8 hours until the sample is dry.

In another preferred embodiment of the method of preparing an oral preparation of the present disclosure, when the concentration of hydroxypropyl-β-cyclodextrin is 10% (w/v) to 30% (w/v), the concentration of KX2-361 or a medicinal salt thereof measured by KX2-361 is 0.5 mg/ml to 6 mg/ml; when the concentration of hydroxypropyl-β-cyclodextrin is 40% (w/v) to 50% (w/v), the concentration of KX2-361 or a medicinal salt thereof measured by KX2-361 is 0.5 mg/ml to 10 mg/ml.

The oral preparation of the present disclosure is a tablet further developed on the basis of the lyophilized powder of the present disclosure. In the present disclosure, the inclusion process is optimized, and the maximum optimization of drug loading is achieved for the drug loading formulation with placement stability, related substances and dissolution of the inclusion solution as the evaluation indicators. Finally, the process that KX2-361 or its medicinal salt (active ingredient) is encapsulated in a solution with pH=1-2 and then the pH value is adjusted back is used, and freeze-drying technique is used to be lyophilized powder to make the inclusion concentration of the active ingredient measured by KX2-361 is up to 10 mg/ml. The oral tablet of the present disclosure achieves high bioavailability. In addition, key indicators such as dissolution and related substances of the tablets are also tested, which are all qualified.

EXAMPLES

Unless otherwise specified, the percentage concentration (%) of each reagent refers to weight (g)/volume (100 mL) percentage concentration (% (w/v)) of the reagent, for example, "the concentration of HP-β-CD is 40%" means that "the concentration of HP-β-CD is 40% (w/v)".

When ethanol is mentioned in the following examples, it refers to a 95% (v/v) ethanol aqueous solution, unless otherwise specified.

Abbreviations are as follows:

KX2-361.BSA: KX2-361.benzene sulfonate

HP-β-CD: hydroxypropyl-β-cyclodextrin

SBE-β-CD: sulfobutyl ether-β-cyclodextrin

API: Active Pharmaceutical Ingredient (hereinafter, it refers to KX2-361.BSA, unless otherwise specified)

PTFE: polytetrafluoroethylene

The purchase information of materials and equipments used in the following examples are as follows:

| Name | Manufacturer/Source | Lot Number |
|---|---|---|
| KX2-361·BSA | ConVerd Co., Ltd, Hangzhou | T1465-07-13-01A |
| hydroxypropyl-β-cyclodextrin | Xi'an DELI Biochemical Industry Co., Ltd | 20140323 |
| 767 type activated carbon for injection | Shanghai Activated Carbon Co., Ltd | 1351011 |
| Cremophor EL | BASF (Germany) | 46736175LO |
| Solutol HS15 | BASF (Germany) | 21464288Q0 |
| Poloxamer 188 | BASF (Germany) | WPMG557C |
| Tween-80 | Croda (UK) | 0000519514 |

| Name | Model | Manufacturer |
|---|---|---|
| Freeze dryer | Lyopro-0.4 | LYOMAC TECHNOLOGY CO., LTD, Shanghai |
| Balance | CP225D | Sartorius (Germany) |
| pH Meter | FE20 | METTLER TOLEDO |
| HPLC | Agilent 1260 | Agilent Co., Ltd (USA) |
| Mass spectrometer | API4000 | AB SCIEX |
| Ultraviolet spectrophotometer | Varian 50Bio | Varian, Inc. (USA) |
| Tablet machine | ZP10A | BEIJING GYLONGLI SCI. & TECH. CO., LTD. |
| Particle counter | GWJ-8 | Tianda Tianfa Technology Co., Ltd. (Tianjin) |
| Disintegration time limit tester | LB-2D type | Shanghai Huanghai Drug Checking Instrument Co., Ltd. |

Example 1

Preparation and Evaluation of KX2-361.Benzene Sulfonate Lyophilized Agent and Redissolved Solution for Injection (the Concentration of HP-β-CD was 30%, and Drug Loading was High)

Prescriptions with the following composition were prepared:

| | HP-β-CD | API | Molar ratio (HP-β-CD:API) KX2-361·BSA | Mass ratio (HP-β-CD:KX2-361) |
|---|---|---|---|---|
| Prescription A1 | 30% | 5 mg/mL | 19-24:1 | 100:1.20 |
| Prescription A2 | 30% | 6 mg/mL | 16-20:1 | 100:1.44 |
| Prescription A3 | 30% | 7 mg/mL | 13-17:1 | 100:1.68 |

Note:
The molecular weight of HP-β-CD is 1431-1806. Therefore, the upper and lower limits of the molecular weight were respectively taken to calculate the molar ratio.

The above-mentioned prescriptions were prepared according to the following steps successively:

1) 1.8 mL concentrated hydrochloric acid was placed in a 200 mL volumetric flask and diluted to 200 mL with distilled water to obtain a hydrochloric acid solution with a pH of about 1.2 (the concentration is 0.1 mol/L, the same below).

2) HP-β-CD was weighed according to the above prescription amounts and added to three 50 mL volumetric flasks respectively. The solution obtained in 1) was added, dissolved by ultrasound (ultrasound frequency is 59 kHz) and diluted to about 46 mL with the above-mentioned hydrochloric acid solution.

3) API (KX2-361 benzene sulfonate) was weighed according to the above prescription amounts and added to the above-mentioned HP-β-CD solutions respectively, and dissolved by ultrasound (ultrasonic frequency is 59 kHz).

4) The pH value of the solution obtained in 3) was adjusted to about 6.0 (±0.05) with 5N NaOH aqueous solution and 0.1N NaOH aqueous solution respectively. The solution was diluted to 50 mL with distilled water.

5) The three prescription solutions each was filtered with a 0.45 μm polyether sulfone filter membrane and dispensed into 10 mL penicillin bottles (dispensed by 2 mL volume per bottle), then freeze-dried.

The freeze-drying curve was as follows:

| Stage | Temperature (° C.) | Vacuum control (Pa) | Time (minute) | Vacuum pump state | Condenser pre-freezing (° C.) |
|---|---|---|---|---|---|
| 1 | −40 | OFF | 5 | OFF | −40 |
| 2 | −40 | OFF | 120 | OFF | |
| 3 | −40 | 20 ± 2 | 360 | ON | |
| 4 | −20 | 20 ± 2 | 360 | ON | |
| 5 | −20 | 10 ± 2 | 360 | ON | |
| 6 | 0 | 10 ± 2 | 360 | ON | |
| 7 | 0 | 10 ± 2 | 360 | ON | |
| 8 | 10 | No control | 360 | ON | |
| 9 | 10 | No control | 120 | ON | |

Sample state after freeze-drying:

The sample had good formability. Lyophilized samples were all pale yellow loose solids.

The lyophilized samples of the above three prescriptions (prescription A1, A2, A3) were redissolved and their redissolution conditions, insoluble particles and dilution stability were evaluated.

1. Redissolving with water and buffered saline solution.

Redissolving method: 2 mL of the following redissolving medium was added to each penicillin bottle of each lyophilized sample, and then turned upside down 30 times, if not dissolved, shaken until dissolved. Timing was started after adding the buffered saline solution, with two repetitions performed simultaneously.

The compositions of the buffer salts were as follows:

| pH (Theoretical value/Actual value) | Ingredient | Theoretical weighing/Actual weighing | Concentration |
|---|---|---|---|
| 4.0/4.00 | Citric acid monohydrate | 210.14 mg/210.5 mg | c = 0.01 mmol/L |
| 5.0/5.00 | Sodium acetate trihydrate | 136.08 mg/137.6 mg | c = 0.01 mmol/L |
| 6.0/6.01 | Sodium dihydrogen phosphate dihydrate | 156.06 mg/156.1 mg | c = 0.01 mmol/L |

Note:
c represented the molar concentration of the solute formulated into a buffer salt.

The redissolving time was shown as follows:

| Redissolving medium with different pH | Prescription A1 | Prescription A2 | Prescription A3 |
|---|---|---|---|
| pH = 4.0 | About 2 minutes | About 2.5 minutes | About 2.5 minutes |
| pH = 5.0 | About 2.5 minutes | About 2.5 minutes | About 2.5 minutes |
| pH = 6.0 | About 2.5 minutes | About 2.5 minutes | About 2.5 minutes |
| Water | About 4 minutes | About 4 minutes | About 4 minutes |

Note:
the redissolving time for each prescription was the average of two repetitions.

Insoluble particles (detection method refers to Light Blockage Method, First Method, Insoluble Particle Inspection Method, 0903, Chinese Pharmacopoeia Part IV, 2015 Edition, the same below) were as follows:

| | | Insoluble particles (1 mL) | | | |
|---|---|---|---|---|---|
| | | 0 hour | | 4 hours | |
| | | ≥10 μm | ≥25 μm | ≥10 μm | >25 μm |
| Prescription A1 | pH = 4.0 | 283 | 42 | 213 | 36 |
| 30% HP-β-CD + | pH = 5.0 | 362 | 63 | 285 | 53 |
| 5 mg/mL API | pH = 6.0 | 597 | 103 | 365 | 28 |
| Prescription A2 | pH = 4.0 | 206 | 29 | 138 | 20 |
| 30% HP-β-CD + | pH = 5.0 | 334 | 30 | 172 | 16 |
| 6 mg/mL API | pH = 6.0 | 427 | 32 | 354 | 19 |
| Prescription A3 | pH = 4.0 | 252 | 43 | 254 | 31 |
| 30% HP-β-CD + | pH = 5.0 | 557 | 160 | 251 | 19 |
| 7 mg/mL API | pH = 6.0 | 739 | 54 | 1003 | 143 |

Note:
For the insoluble particle, the result was the average of results obtained by detecting two samples, with measuring the insoluble particles after 0 hour and 4 hours respectively.

From the above results, it can be found that when the samples containing 30% HP-β-CD were redissolved with buffer salts of different pH values, the redissolving time was reduced to about 2.5 minutes from about 4 minutes when redissolved with pure water. When the samples containing 30% HP-β-CD were redissolved with buffer salt of pH=4.0, the insoluble particles conditions were good, wherein the insoluble particles conditions were good when the prescription A2 was redissolved with the three buffer salts respectively.

In addition, according to the Chinese Pharmacopoeia Standard, the number of insoluble particles of ≥10 μm in any container of less than 100 mL shall not exceed 6000, and the number of insoluble particles of ≥25 μm shall not exceed 600. Since the test results of the insoluble particles shown in the above table were the detection values of 1 mL solution, the prescriptions A1-A3 are all suitable for further prepared into a pharmaceutical preparation product which is volume amplified (consider the specifications of the drug according to its effectiveness and safety) and can reach larger single dose and meets the Chinese Pharmacopoeia Standard.

2. Redissolving with 5% glucose aqueous solution and 0.9% sodium chloride aqueous solution.

Redissolving method: 2 mL of the following redissolving media were added to each penicillin bottle of each lyophilized sample, and then turned upside down 30 times, and if not dissolved, shaken until dissolved. Timing was started after the redissolving media were added, and two repetitions were performed simultaneously.

The redissolving time was shown as follows:

| Redissolving medium | Prescription A1 | Prescription A2 | Prescription A3 |
|---|---|---|---|
| 5% glucose aqueous solution | About 3 minutes | About 3 minutes | About 3 minutes |
| 0.9% sodium chloride aqueous solution | About 3 minutes | About 3 minutes | About 3 minutes |

Note:
the redissolving time for each prescription was the average of two repetitions.

Insoluble particles were shown as follows:

| | | Insoluble particles (1 mL) | | | |
|---|---|---|---|---|---|
| | | 0 hour | | 4 hours | |
| Prescription number | Redissolving medium | ≥10 μm | ≥25 μm | ≥10 μm | ≥25 μm |
| Prescription A1 30% HP-β-CD + 5 mg/mL API | 5% glucose aqueous solution | 361 | 28 | 269 | 47 |
| | 0.9% sodium chloride aqueous solution | 277 | 56 | 236 | 32 |

-continued

| Prescription number | Redissolving medium | Insoluble particles (1 mL) | | | |
|---|---|---|---|---|---|
| | | 0 hour | | 4 hours | |
| | | ≥10 μm | ≥25 μm | ≥10 μm | ≥25 μm |
| Prescription A2 30% HP-β-CD + 6 mg/mL API | 5% aqueous glucose solution | 407 | 113 | 322 | 30 |
| | 0.9% aqueous sodium chloride solution | 919 | 348 | 282 | 59 |
| Prescription A3 30% HP-β-CD + 7 mg/mL API | 5% glucose aqueous solution | 434 | 47 | 396 | 82 |
| | 0.9% sodium chloride aqueous solution | 456 | 76 | 386 | 55 |

Note:
For the insoluble particles, the result was the average of the results obtained by detecting two samples, with measuring the insoluble particles after 0 hour and 4 hours respectively.

The above results indicate that the effect of redissolving with buffered saline solution of pH 4.0 is better than that of redissolving with 5% glucose aqueous solution and redissolving with 0.9% sodium chloride aqueous solution.

Example 2

Preparation and Evaluation of KX2-361.Benzene Sulfonate Lyophilized Agent and Redissolving Solution for Injection (the Concentration of HP-β-CD was 30%, and Drug Loading was Low)

Prescriptions with the following compositions were prepared:

| | HP-β-CD | API | Molar ratio (HP-β-CD:API) | Final pH value | Mass ratio (HP-β-CD:KX2-361) |
|---|---|---|---|---|---|
| Prescription A4 | 30% | 2 mg/mL | 47-59:1 | 6.0 | 100:0.48 |
| Prescription A5 | 30% | 2 mg/mL | 47-59:1 | 4.0 | 100:0.48 |
| Prescription A6 | 30% | 2 mg/mL | 47-59:1 | 4.0 (adjusted with 10 mM citric acid saline solution) | 100:0.48 |

Note:
The molecular weight of HP-β-CD was 1431-1806. Therefore, the upper and lower limits of the molecular weight were respectively taken to calculate the molar ratio.

The above-mentioned prescriptions were prepared according to the following steps successively:

1) 1.8 mL concentrated hydrochloric acid was placed in a 200 mL volumetric flask and diluted to 200 mL with distilled water to obtain a hydrochloric acid solution with a pH value of about 1.2.

2) HP-β-CD was weighed according to the above prescription amounts and added to three 25 mL volumetric flasks respectively. The solution obtained in 1) was added, dissolved by ultrasound (ultrasound frequency is 59 kHz) and diluted to about 23 mL with the above hydrochloric acid solution.

3) API was weighed according to the above prescription amounts, and added to the above HP-β-CD solution, respectively. For the prescription A6, 50.7 mg of citric acid was added and dissolved by ultrasound (ultrasonic frequency is 59 kHz).

4) The pH value of the solution obtained in 3) was adjusted to the pH values (±0.05) shown in the above table with 5N NaOH aqueous solution and 0.1N NaOH aqueous solution. The solution was diluted to 25 mL with distilled water.

5) The three prescription solutions were filtered with a 0.45 μm polyether sulfone filter membrane and dispensed into 10 mL penicillin bottles (2 mL per bottle), then freeze-dried.

| Stage | Temperature (° C.) | Vacuum control (Pa) | Time (minute) | Vacuum pump state | Condenser pre-freezing (° C.) |
|---|---|---|---|---|---|
| 1 | −40 | OFF | 5 | OFF | −40 |
| 2 | −40 | OFF | 120 | OFF | |

-continued

| Stage | Temperature (° C.) | Vacuum control (Pa) | Time (minute) | Vacuum pump state | Condenser pre-freezing (° C.) |
|---|---|---|---|---|---|
| 3 | −40 | 20 ± 2 | 360 | ON | |
| 4 | −20 | 20 ± 2 | 360 | ON | |
| 5 | −20 | 10 ± 2 | 360 | ON | |
| 6 | 0 | 10 ± 2 | 360 | ON | |
| 7 | 0 | 10 ± 2 | 360 | ON | |
| 8 | 10 | No control | 360 | ON | |
| 9 | 10 | No control | 120 | ON | |

Sample state after freeze-drying: the samples had good formability. Lyophilized samples were all fluffy snow-like solids.

The lyophilized samples of the above three prescriptions (prescriptions A4, A5, A6) were redissolved and their redissolving conditions and insoluble particles conditions in 5% glucose aqueous solution and physiological saline were evaluated.

Redissolving method: 2 mL of the following redissolving medium was added to each penicillin bottle of each lyophilized sample, and then turned upside down 30 times, and if not dissolved, shaken until dissolved. Started timing after the redissolving medium was added, and measured two samples repeatedly. The redissolving time was shown as follows:

| Redissolving medium | Prescription A4 | Prescription A5 | Prescription A6 |
|---|---|---|---|
| 5% glucose aqueous solution | About 3 minutes | About 3 minutes | About 3 minutes |
| 0.9% sodium chloride aqueous solution | About 3 minutes | About 3 minutes | About 3 minutes |

Note: for each prescription, the redissolving time was the average of the detection results of two samples.

Insoluble particles were shown as follows:

| Prescription number | Redissolving medium | Insoluble particles (1 mL) | | | |
|---|---|---|---|---|---|
| | | 0 hour | | 4 hours | |
| | | ≥10 μm | ≥25 μm | ≥10 μm | ≥25 μm |
| Prescription A4 | 5% glucose aqueous solution | 175 | 25 | 177 | 18 |
| Prescription A5 | 5% glucose aqueous solution | 138 | 12 | 157 | 38 |
| Prescription A6 | 5% glucose aqueous solution | 160 | 16 | 154 | 32 |

Note: For the insoluble particles, the result was the average of the results obtained by detecting two samples respectively.

The lyophilized samples of the above three prescriptions (prescriptions A4, A5, and A6) were redissolved with the redissolving medium as shown in the following table, and redissolved drug solution was diluted in the same medium according to a certain ratio, and the dilution ratio (redissolved solution volume: dilution medium volume) was 1:2, 1:5, 1:10, respectively. The insoluble particles at 0 and 4 hours were detected for diluted solution. Diluted insoluble particles are shown as follows:

| Prescription number | Redissolving medium | Dilution medium | Dilution ratio (volume ratio) | Insoluble particles (1 mL) | | | |
|---|---|---|---|---|---|---|---|
| | | | | 0 hour | | 4 hours | |
| | | | | ≥10 μm | ≥25 μm | ≥10 μm | ≥25 μm |
| Prescription A4 | 0.9% sodium chloride aqueous solution | 0.9% sodium chloride aqueous solution | 1:2 | 72 | 8 | 82 | 5 |
| | | | 1:5 | 43 | 1 | 28 | 0 |
| | | | 1:10 | 27 | 1 | 36 | 1 |
| | 5% glucose aqueous solution | 5% glucose aqueous solution | 1:2 | 107 | 16 | 90 | 13 |
| | | | 1:5 | 46 | 4 | 49 | 5 |
| | | | 1:10 | 30 | 3 | 56 | 5 |
| Prescription A5 | 0.9% sodium chloride aqueous solution | 0.9% sodium chloride aqueous solution | 1:2 | 87 | 8 | 48 | 4 |
| | | | 1:5 | 31 | 0 | 26 | 0 |
| | | | 1:10 | 49 | 0 | 34 | 4 |
| | 5% glucose aqueous solution | 5% glucose aqueous solution | 1:2 | 63 | 8 | 66 | 9 |
| | | | 1:5 | 31 | 0 | 41 | 0 |
| | | | 1:10 | 58 | 2 | 44 | 7 |
| Prescription A6 | 0.9% sodium chloride aqueous solution | 0.9% sodium chloride aqueous solution | 1:2 | 106 | 21 | 78 | 3 |
| | | | 1:5 | 36 | 6 | 33 | 3 |
| | | | 1:10 | 30 | 0 | 30 | 3 |
| | 5% glucose aqueous solution | 5% glucose aqueous solution | 1:2 | 75 | 13 | 138 | 18 |
| | | | 1:5 | 31 | 0 | 25 | 1 |
| | | | 1:10 | 34 | 0 | 47 | 1 |

Note: For the insoluble particle, the result was the average of the results obtained by detecting two samples, with measuring the insoluble particles after 0 hour and 4 hours respectively.

It can be seen from the dilution of the above samples that no API precipitated in 4 hours. All of the three prescriptions have the potential to be intravenously dripped as drug solutions after diluted by adding a filter.

High drug loading formulation A2 and low drug loading formulation A5 with 30% HP-β-CD concentration were selected for the following tests.

Test Example 1

Measurement of Insoluble Particles and Osmotic Pressure after Placing 8 Days

According to the methods described in Example 1 and Example 2, prescription A2 and prescription A5 were prepared anew in batches of 200 mL. After the lyophilized samples of prescription A2 (30% HP-β-CD+6 mg/mL API) and prescription A5 (30% HP-β-CD+2 mg/mL API) were stored at 4° C. for 8 days, insoluble particles were detected and the results are as follows:

| Prescription | Redissolving medium (2 ml) | Storage Conditions | Insoluble particles (1 mL) n = 10 0 hour | |
|---|---|---|---|---|
| | | | ≥10 μm | ≥25 μm |
| Prescription A5 30% HP-β-CD + 2 mg/mL API | Distilled water | 4° C. | 206 | 10 |
| Prescription A2 30% HP-β-CD + 6 mg/mL API | Distilled water | 4° C. | 136 | 8 |

Note:
n = 10 represents that 10 samples were detected for each prescription, and the result of insoluble particles was the average of the results obtained by detecting 10 samples respectively.

The results in the above table shows that after lyophilized powder of two prescriptions were stored at 4° C. for 8 days, the insoluble particles were still qualified after redissolving.

Infusion of isotonic solution to the elderly and infant patients with poor kidney and cardiopulmonary function may easily cause electrolyte retention and severe complications such as edema and the like, therefore, isotonic infusion is referred to as "dangerous infusion" in pediatric clinic. Since continuous water loss in the forms such as evaporation of body surface, lung exhalation and the like, generally, the safety range of the hypotonic infusion zone is relatively wide, the safety margin of the hypotonic infusion volume is relatively large, and the use range of the hypotonic infusion is relatively broad. Therefore, dilution stability tests and osmotic pressure measurements were performed with hypotonic solutions. Lyophilized sample of prescription A5 (30% HP-β-CD+2 mg/mL API) was taken, and diluted using a hypotonic solution (0.45% sodium chloride aqueous solution and 2.5% glucose aqueous solution) with different ratios after redissolving with 2 mL distilled water for each penicillin bottle. Insoluble particles and osmotic pressure were measured.

The results are as follows:

| | | | Insoluble particles (1 mL) | | | |
|---|---|---|---|---|---|---|
| | | Dilution ratio | 0 h | | 4 h | |
| Prescription | Dilution medium | (volume ratio) | ≥10 μm | ≥25 μm | ≥10 μm | ≥25 μm |
| Prescription A5 | 0.45% sodium chloride aqueous solution | 1:1 | 33 | 5 | 33 | 6 |
| | | 1:5 | 30 | 2 | 13 | 2 |
| | | 1:10 | 34 | 3 | 27 | 4 |
| | 2.5% glucose aqueous solution | 1:1 | 64 | 9 | 26 | 7 |
| | | 1:5 | 60 | 10 | 18 | 2 |
| | | 1:10 | 42 | 9 | 11 | 2 |

Note:
For the insoluble particle, the result was the average of the results obtained by detecting two samples, with measuring the insoluble particles after 0 hour and 4 hours respectively.

Osmotic pressure measurement results are as follows:

| Prescription | Dilution medium | Dilution ratio (volume ratio) | Osmotic pressure (mOsm) |
|---|---|---|---|
| Prescription A5 | 0.45% sodium chloride aqueous solution | 1:1 | 250 |
| | | 1:5 | 170 |
| | | 1:10 | 157 |
| | 2.5% glucose aqueous solution | 1:1 | 264 |
| | | 1:5 | 168 |
| | | 1:10 | 157 |

Note:
For the osmotic pressure, the result was the average of the results obtained by detecting two samples.

The osmolarity of the isotonic solution is generally 280-320 mOsm, and it can be seen that the solution has low osmotic pressure and its insoluble particle test results are better after the prescription A5 has been diluted with different ratios.

Test Example 2

3-Month Stability Study

Lyophilized samples of prescriptions A2 and A5 were placed in a thermostatic chamber at 25° C. and 40° C. for 3 months for stability study. For each condition, two samples were taken to investigate API content %, related substances (i.e., substances obtained from API degradation) with HPLC, and to investigate insoluble particles, see Table 1 and Table 2.

The HPLC measurement conditions for the content and related substances were as follows:

| | |
|---|---|
| Chromatographic Column | Waters Symmetry C18 100 4.6 mm, 3.5 um |
| Mobile Phase A | 0.1% TFA-water |
| Mobile Phase B | 60% acetonitrile/40% ethanol |
| Diluent | 50% water/50% acetonitrile |

| Mobile Phase | Time (minute) | % A | % B |
|---|---|---|---|
| | 0.0 | 95 | 5 |
| | 20.0 | 30 | 70 |
| | 25.0 | 0 | 100 |
| | 27.0 | 0 | 100 |
| | 27.1 | 95 | 5 |
| | 35.0 | 95 | 5 |

| | |
|---|---|
| Flow rate | 1.0 mL/minute |
| Column temperature (° C.) | 25° C. |
| Sample volume | 10 ul |
| Sample plate temperature | 5° C. |
| Detection wavelength | 261 nm |

TABLE 1

Stability study of lyophilized preparations for 3 months - content % and total impurity %

| | Total impurity % | Content % | Average content % |
|---|---|---|---|
| Prescription A5-25° C.-0 M | 0.39 | 105.76 | 105.2 |
| | 0.38 | 104.72 | |
| Prescription A5-25° C.-3 M | 0.48 | 102.24 | 104.5 |
| | 0.50 | 106.72 | |
| Prescription A5-40° C.-3 M | 0.51 | 99.09 | 99.8 |
| | 0.49 | 100.60 | |
| Prescription A2-25° C.-0 M | 0.35 | 106.62 | 106.4 |
| | 0.36 | 106.25 | |
| Prescription A2-25° C.-3 M | 0.52 | 106.42 | 105.7 |
| | 0.46 | 104.94 | |
| Prescription A2-40° C.-3 M | 0.55 | 104.95 | 105.1 |
| | 0.59 | 105.23 | |

As we can see from the above table, the content of the two lyophilized powders remained unchanged for 3 months, and according to the impurity profile, three new degradation impurities appeared, and the total amount of impurities increased slightly, but they were all within acceptable range.

The samples at the time points shown in Table 2 for prescription A2 and prescription A5 placed at 25° C. and 40° C. within three months were taken for detecting insoluble particles, as shown in the table below for details:

TABLE 2

Stability investigation of lyophilized preparations for 3 months-insoluble particles

| Prescription (2 ml) | Redissolving medium | Time | Insoluble particles (1 mL) n = 2 | | | |
|---|---|---|---|---|---|---|
| | | | 25° C. | | 40° C. | |
| | | | ≥10 μm | ≥25 μm | ≥10 μm | ≥25 μm |
| Prescription A5 | Distilled water | One month | 83 | 14 | 89 | 16 |
| | | Two months | 43 | 7 | 82 | 13 |
| | | Three months | 88 | 21 | 147 | 40 |
| Prescription A2 | Distilled water | One month | 138 | 24 | 188 | 41 |
| | | Two months | 105 | 13 | 259 | 55 |
| | | Three months | 84 | 12 | 118 | 21 |

Note:
n = 2 represents that 2 samples were detected for each prescription, and the result of insoluble particles is the average of the results obtained by detecting 2 samples respectively.

It can be seen that both prescriptions are placed at 25° C. and 40° C. for 3 months respectively, and the test results of insoluble particles are good.

Test Example 3

Dynamic Adsorption Test

The lyophilized samples of prescription A2 and prescription A5 were redissolved by adding water for injection, the prescription A2 was formulated as a solution with drug concentration of 6 mg/mL, and the prescription A5 was formulated as a solution with drug concentration of 2 mg/mL, and then the state of injection into blood vessels was simulated, the physical stability under physiological conditions was investigated, and the possibility of precipitation after intravenous administration was speculated.

1. Test Operation: Using peristaltic pump to make 5% BSA (bovine serum albumin) to pass through a flexible tube (Longerpump, 14#) with 1.6 mm inner diameter at a flow rate of 5 ml/min. The redissolved drug solution was injected into the flexible tube by inserting a needle which was 30 cm away from the end of the flexible tube, and the injection rate of sample was controlled by syringe pump, and the injection rate was 0.2-5 ml/min (see Table 3). After the drug solution and 5% BSA solution were mixed at a certain rate, the effluent was received at the end of the flexible tube:

(1) 4 ml of effluent was taken to measure the absorbance value at 540 nm with an UV spectrophotometer and detect the presence of precipitate, and the mixed solution of blank preparation (30% hydroxypropyl-β-cyclodextrin solution) and 5% BSA serves as a control;

(2) 1 ml of effluent was taken in which 9 ml of acetonitrile was added, whirled for 5 minutes, and filtered with a 0.45 μm nylon filter membrane, and then subsequent filtrate was taken as a sample with 100% concentration for HPLC detection.

4 ml of effluent was taken and filtered with 0.45 μm PES filter membrane, and 1 ml of the subsequent filtrate was taken in which 9 ml of acetonitrile was added, whirled for 5 minutes, and filtered with 0.45 μm nylon membrane, and then 1 ml of the subsequent filtrate was taken as a sample to be tested for HPLC detection. The ratio of the sample to be tested to the sample with 100% concentration is the proportion of the unprecipitated API in the sample.

2. Test Results:

TABLE 3

Dynamic precipitation test results (n = 2)

| Sample | Injection rate (ml/min) | Phenomenon | Ultraviolet Absorption (Abs) | Proportion of unprecipitated drug (%) |
|---|---|---|---|---|
| Prescription A2 | 0.2 | No visible precipitation | 0.003 ± 0.004 | 102.6 ± 3.2 |
|  | 1.0 |  | 0.006 ± 0.000 | 100.5 ± 0.6 |
|  | 5.0 |  | −0.005 ± 0.001 | 100.4 ± 1.8 |
| Prescription A5 | 0.2 |  | 0.004 ± 0.001 | 103.2 ± 2.5 |
|  | 1.0 |  | 0.006 ± 0.001 | 101.6 ± 4.0 |
|  | 5.0 |  | −0.006 ± 0.001 | 100.9 ± 1.8 |

Note:

n = 2 represents that 2 samples were detected for each prescription, and the test result is the average of the results obtained by detecting 2 samples respectively.

The results of the detection of the precipitate and drug content are shown in the above table. It can be seen from the results that, the UV absorbance of each group was very low, indicating that no significant precipitation occurred for the three preparations after injecting 5% BSA at different rates. After the sample effluent was filtered, the drug was almost remained in the filtrate, indicating that the drug was not precipitated.

From the results of this test, it can be seen that prescription A2 and prescription A5 investigated in the test have good compatibility with simulated plasma, and low risk of precipitation after intravenous drip or bolus.

Test Example 4

Static Adsorption Test

A static adsorption experiment was conducted to verify the conclusion of the dynamic adsorption experiment more fully.

Diluent 1 was PBS (phosphate buffer solution of pH 7.4) containing 50 mmol/L $NaH_2PO_4$, and BSA (bovine serum albumin) was dissolved with this diluent 1 to prepare 5% BSA diluent 2.

Lyophilized samples of prescription A5 (30% HP-β-CD+2 mg/mL API, final pH=4.0) and prescription A2 (30% HP-β-CD+6 mg/mL API, final pH=6.0) were taken and redissolved with 2 mL of distilled water, respectively, and then diluted different dilution times (volume ratios) with the above diluent 1 and diluent 2 to observe whether samples were precipitated. The dilute test at each dilution times was repeated once. The results were as follows:

| Prescription | Dilution medium | Dilution times | Results |
|---|---|---|---|
| Prescription A5 | PBS diluent | 1:1 | No obvious precipitation within 2 hours |
|  |  | 1:5 | No obvious precipitation within 2 hours |
|  |  | 1:10 | No obvious precipitation within 2 hours |

-continued

| Prescription | Dilution medium | Dilution times | Results |
|---|---|---|---|
|  | BSA diluent | 1:1 | No obvious precipitation within 2 hours |
|  |  | 1:5 | No obvious precipitation within 2 hours |
|  |  | 1:10 | No obvious precipitation within 2 hours |
| Prescription A2 | PBS diluent | 1:1 | No obvious precipitation within 2 hours |
|  |  | 1:5 | Solid precipitation after 30 minutes |
|  |  | 1:10 | Solid precipitation after 20 minutes |
|  | BSA diluent | 1:1 | No obvious precipitation within 2 hours |
|  |  | 1:5 | No obvious precipitation within 2 hours |
|  |  | 1:10 | No obvious precipitation within 2 hours |

The experiment results showed that no significant solid precipitation occurred after the prescription A5 was diluted in different ratios with PBS (pH=7.4) and PBS containing 5% BSA (pH=7.4). This result further verified that the prescription A5 could be administered by intravenous drip after diluted within 10 times.

When the prescription A2 was diluted in the ratios of 1:5 and 1:10 with PBS (pH=7.4) (diluent 1), solid was precipitated within half an hour, while diluted in same ratios with PBS (pH=7.4) (diluent 2) containing 5% BSA, no obvious precipitation occurs within 2 hours. After 16 hours, a large amount of solids were precipitated in the dilution group of diluent 1, while less solids were precipitated in the dilution group of diluent 2. The experiment results showed that BSA prevented the drug precipitation by combination with a portion of drug. The results of the dynamic adsorption test showed that no drug precipitation occurs for the prescription A2 at different drip rates. Therefore, it is considered that the use of intravenous bolus (bolus 11.6 mL, bolus for 2-3 minutes) is feasible when this prescription is administered at a dose of 69.5 mg.

Example 3

Preparation and Evaluation of KX2-361.Benzene Sulfonate Lyophilized Agent and Redissolving Solution for Injection (the Concentration of HP-β-CD was 20%, Drug Loading was High)

Prescriptions with the following compositions were prepared:

|  | HP-β-CD | API | Molar ratio (HP-β-CD:API) | Mass ratio (HP-β-CD:KX2-361) |
|---|---|---|---|---|
| Prescription A7 | 20% | 3 mg/mL | 21-26:1 | 100:1.08 |
| Prescription A8 | 20% | 4 mg/mL | 16-20:1 | 100:1.44 |

Note:
The molecular weight of HP-β-CD was 1431-1806. Therefore, the upper and lower limits of the molecular weight were respectively taken to calculate the molar ratio.

The above-mentioned prescriptions were prepared according to the following steps successively:

1) 1.8 mL concentrated hydrochloric acid was placed in a 200 mL volumetric flask and diluted to 200 mL with distilled water to obtain a hydrochloric acid solution with a pH value of about 1.2.

2) HP-β-CD was weighed according to the above prescription amounts and added into two 25 mL volumetric flasks, respectively. The solution obtained in 1) was added, dissolved by ultrasound (ultrasound frequency was 59 kHz) and diluted to about 23 mL with the above hydrochloric acid solution.

3) API was weighed according to the above prescription amounts and added to the above HP-β-CD solution, respectively, and dissolved by ultrasound (ultrasonic frequency was 59 kHz).

4) The pH of the solution obtained in 3) was adjusted to about 6.0 (±0.05) with 5N NaOH aqueous solution and 0.1N NaOH aqueous solution respectively. The solution was diluted to 25 mL with distilled water.

5) The two prescription solutions were filtered with a 0.45 μm polyether sulfone filter membrane and dispensed into 10 mL penicillin bottles (dispensed by 2 mL volume per bottle), and freeze-dried.

The freeze-drying curve was as follows:

| Stage | Temperature (° C.) | Vacuum control (Pa) | Time (minute) | Vacuum pump state | Condenser pre-freezing (° C.) |
|---|---|---|---|---|---|
| 1 | -40 | OFF | 5 | OFF | -40 |
| 2 | -40 | OFF | 120 | OFF | |
| 3 | -40 | 20 ± 2 | 360 | ON | |
| 4 | -20 | 20 ± 2 | 360 | ON | |
| 5 | -20 | 10 ± 2 | 360 | ON | |
| 6 | 0 | 10 ± 2 | 360 | ON | |
| 7 | 0 | 10 ± 2 | 360 | ON | |
| 8 | 10 | No control | 360 | ON | |
| 9 | 10 | No control | 120 | ON | |

Sample state after freeze-drying: the samples had good formability. Lyophilized samples were all white fluffy snow-like solids.

The lyophilized samples of the above two prescriptions (prescriptions A7 and A8) were redissolved and their redissolving status and insoluble particles were evaluated.

Redissolving method: 2 mL of water and the following buffered saline solution were added to each penicillin bottle of each lyophilized sample, and then turned upside down 30 times, and if not dissolved, shaken until dissolved. Timing was started after the redissolving medium was added, and two repetitions were performed simultaneously.

The compositions of the buffer salt were as follows:

| pH (Theoretical value/Actual value) | Ingredient | Theoretical weighing/Actual weighing | Concentration |
|---|---|---|---|
| 4.0/4.00 | Citric acid monohydrate | 210.14 mg/211.4 mg | c = 0.01 mmol/L |
| 5.0/5.01 | Sodium acetate trihydrate | 136.08 mg/137.4 mg | c = 0.01 mmol/L |
| 6.0/6.00 | Sodium dihydrogen phosphate dihydrate | 156.06 mg/156.6 mg | c = 0.01 mmol/L |

The redissolving time was shown as follows:

| Redissolving medium with different pH | Prescription A7 | Prescription A8 |
|---|---|---|
| pH = 4.0 | About 1.5 minutes | About 1.5 minutes |
| pH = 5.0 | About 1.5 minutes | About 1.5 minutes |
| pH = 6.0 | About 1.5 minutes | About 1.5 minutes |
| Water | About 3 minutes | About 3 minutes |

Note:
the redissolving time for each prescription was the average of two repetitions.

Insoluble particles were shown as follows:

| | | Insoluble particles (1 mL) | | | |
|---|---|---|---|---|---|
| | | 0 hour | | 4 hours | |
| | | ≥10 μm | ≥25 μm | ≥10 μm | ≥25 μm |
| Prescription A7 | pH = 4.0 | 641 | 127 | 370 | 54 |
| | pH = 5.0 | 490 | 56 | 249 | 27 |
| | pH = 6.0 | 435 | 47 | 285 | 36 |
| Prescription A8 | pH = 4.0 | 192 | 11 | 138 | 19 |
| | pH = 5.0 | 328 | 25 | 224 | 27 |
| | pH = 6.0 | 660 | 182 | 218 | 45 |

Note:
The insoluble particles of each prescription were measured by combining two bottles, with measuring after 0 and 4 hours respectively.

From the above results, it can be found that when the sample containing 20% HP-β-CD was redissolved with buffer salts of different pH values, the redissolving time was reduced to about 1.5 minutes from about 3 minutes when redissolved with pure water. Moreover, the test results of the insoluble particles of prescription A8 redissolved in the buffered saline solutions of pH 4.0 and pH 5.0 were more superior than those of prescription A7.

Example 4

Preparation and Evaluation of KX2-361.Benzene Sulphonate Lyophilized Agent and Redissolving Solution for Injection (the Concentration of HP-β-CD was 20%, Drug Loading was Low, and an Inclusion pH Value was 1.2)

A prescription with the following composition was prepared:

| | HP-β-CD | API | Molar ratio (HP-β-CD:API) | Mass ratio (HP-β-CD:KX2-361) | Inclusion pH value | Final pH value |
|---|---|---|---|---|---|---|
| Prescription A9 | 20% | 2 mg/mL | 31-39:1 | 100:0.72 | 1.2 | 4.0 |

Note:
The molecular weight of HP-β-CD was 1431-1806. Therefore, the upper and lower limits of the molecular weight were respectively taken to calculate the molar ratio.

The above prescription was prepared according to the following steps successively:

1) 1.8 mL concentrated hydrochloric acid was placed in a 200 mL volumetric flask and diluted to 200 mL with distilled water to obtain a hydrochloric acid solution with pH=1.21.

2) HP-β-CD was weighed according to the above prescription amount and added to 25 mL volumetric flask. The solution obtained in 1) was added, dissolved by ultrasound (ultrasound frequency was 59 kHz) and diluted to about 23 mL with the above hydrochloric acid solution.

3) API was weighed according to the above prescription amount and added to the above HP-β-CD solution, and dissolved by ultrasound (ultrasonic frequency was 59 kHz).

4) The pH value of the solution obtained in 3) was adjusted to about 4.0 (±0.05) with 5N NaOH aqueous solution and 0.1N NaOH aqueous solution. The solution was diluted to 25 mL with distilled water.

5) The prescription solution was filtered with a 0.45 μm polyether sulfone filter membrane and dispensed into 10 mL penicillin bottles (2 mL per bottle), and freeze-dried.

The freeze-drying curve was as follows:

| Stage | Temperature (° C.) | Vacuum control (Pa) | Time (minute) | Vacuum pump state | Condenser pre-freezing (° C.) |
|---|---|---|---|---|---|
| 1 | −40 | OFF | 5 | OFF | −40 |
| 2 | −40 | OFF | 120 | OFF | |
| 3 | −40 | 20 ± 2 | 360 | ON | |
| 4 | −20 | 20 ± 2 | 360 | ON | |
| 5 | −20 | 10 ± 2 | 360 | ON | |
| 6 | 0 | 10 ± 2 | 360 | ON | |
| 7 | 0 | 10 ± 2 | 360 | ON | |
| 8 | 10 | No control | 360 | ON | |
| 9 | 10 | No control | 120 | ON | |

Sample state after freeze-drying: the sample had good formability. Lyophilized sample was pale yellow fluffy snow-like solids.

Two penicillin bottles of the lyophilized sample of prescription A9 were taken and redissolved with 2 mL of physiological saline (i.e., 0.9% sodium chloride aqueous solution) and 5% glucose aqueous solution, and then diluted with the corresponding solution to detect insoluble particles, and the dilute test at each dilution times was repeated once. The results were as follows:

| | Redissolving medium | Dilution medium | Dilution ratio (volume ratio) | Insoluble particles (1 mL) 0 hour ≥10 μm | ≥25 μm | 4 hours ≥10 μm | ≥25 μm |
|---|---|---|---|---|---|---|---|
| Prescription A9 | Physiological saline | Physiological saline | 1:2 | 108 | 11 | No solid precipitation | |
| | | | 1:5 | 93 | 19 | Solid precipitated out after 2.5 h | |
| | | | 1:10 | 76 | 12 | | |
| | 5% glucose aqueous solution | 5% glucose aqueous solution | 1:2 | 89 | 20 | No solid precipitation | |
| | | | 1:5 | 122 | 19 | Solid precipitation after 2.5 h | |

Note:
For the insoluble particles, the result was the average of the results obtained by detecting two samples, with measuring the insoluble particles after 0 hour and 4 hours, respectively.

From the above table, it can be seen that, after prescription A9 was dissolved, the solution obtained by diluting within 2 times with same medium had good stability, while the systems obtained by multi-fold dilution were unstable and easy to precipitate solids. Therefore, prescription A9 can be administered directly after redissolution, it also can be administered after being redissolved and diluted within 2 times by volume.

Example 5

Preparation and Evaluation of KX2-361.Benzene Sulphonate Lyophilized Preparation for Injection (the Concentration of HP-β-cd Was 20%, the Drug Loading was Low, and an Inclusion pH Value was 2)

Prescriptions with the following composition were prepared:

|  | HP-β-CD | API | Molar ratio (HP-β-CD:API) | Mass ratio (HP-β-CD:KX2-361) | Inclusion pH value | Final pH value |
|---|---|---|---|---|---|---|
| Prescription A10 | 20% | 2 mg/mL | 31-39:1 | 100:0.72 | 2.0 | 4.0 |
| Prescription A11 | 20% | 1.5 mg/mL | 42-53:1 | 100:0.54 | 2.0 | 4.0 |

Note:
The molecular weight of HP-β-CD was 1431-1806. Therefore, the upper and lower limits of the molecular weight were respectively taken to calculate the molar ratio.

The above prescriptions were prepared according to the following steps successively:

1) 0.18 mL concentrated hydrochloric acid was placed in a 200 mL volumetric flask and diluted to 200 mL with distilled water to obtain a hydrochloric acid solution with pH=2.03.

2) HP-β-CD was weighed according to the above prescription amounts and added to a 25 mL volumetric flask respectively. The solution obtained in 1) was added, dissolved by ultrasound (ultrasound frequency was 59 kHz) and diluted to about 23 mL with the above hydrochloric acid solution.

3) The API was weighed according to the above prescription amounts, and added to the above HP-β-CD solutions, respectively, and dissolved by stirring at 40° C. for about 1.5 hours (prescription 10) and 1 hour (prescription 11) respectively.

4) The pH value of the solution obtained in 3) was adjusted to about 4.0 (±0.05) with 5N NaOH aqueous solution and 0.1N NaOH aqueous solution respectively. The solution was diluted to 25 mL with distilled water.

5) The two prescription solutions were filtered with a 0.45 μm polyether sulfone filter membrane and dispensed into 10 mL penicillin bottles (2 mL per bottle), and freeze-dried.

The freeze-drying curve was as follows:

| Stage | Temperature (° C.) | Vacuum control (Pa) | Time (minute) | Vacuum pump state | Condenser pre-freezing (° C.) |
|---|---|---|---|---|---|
| 1 | −40 | OFF | 5 | OFF | −40 |
| 2 | −40 | OFF | 120 | OFF | |
| 3 | −40 | 20 ± 2 | 360 | ON | |
| 4 | −20 | 20 ± 2 | 360 | ON | |
| 5 | −20 | 10 ± 2 | 360 | ON | |
| 6 | 0 | 10 ± 2 | 360 | ON | |
| 7 | 0 | 10 ± 2 | 360 | ON | |
| 8 | 10 | No control | 360 | ON | |
| 9 | 10 | No control | 120 | ON | |

Sample state after freeze-drying: the samples had good formability. The lyophilized samples were pale yellow and near white fluffy snow-like solids.

Test Example 5

Study on the Properties of Prescriptions A9-A11

1. Redissolving Test and Inspection of Insoluble Particles

This test example investigated the redissolving and insoluble particles of prescriptions A9-A11 in 5% glucose aqueous solution, distilled water and physiological saline (i.e., 0.9% sodium chloride injection).

Redissolving method: redissolving media having the following volumes were added to each penicillin bottle of each lyophilized sample, respectively, and then turned upside down 30 times, and if not dissolved, shaken until dissolved. Timing was started after the redissolving media were added.

The redissolving time was shown as follows:

|  | Prescription A9 | Prescription A10 | Prescription A11 |
|---|---|---|---|
| Distilled water (4 mL) | About 1.5 minutes | About 1.5 minutes | About 1.5 minutes |
| 5% aqueous glucose solution (2 mL) | About 2 minutes | About 2 minutes | About 2 minutes |
| Physiological saline (2 mL) | About 2 minutes | About 2 minutes | About 2 minutes |

Insoluble particles were shown as follows:

| Prescription | Redissolving medium | Insoluble particles (1 mL) | | | |
|---|---|---|---|---|---|
| | | 0 hour | | 4 hours | |
| | | ≥10 μm | ≥25 μm | ≥10 μm | ≥25 μm |
| Prescription A9 | Distilled water | 154 | 4 | 111 | 10 |
| | 5% glucose aqueous solution | 253 | 24 | 142 | 21 |
| | Physiological saline | 192 | 12 | 201 | 39 |
| Prescription A10 | Distilled water | 262 | 19 | 129 | 21 |
| | 5% glucose aqueous solution | 335 | 39 | 186 | 30 |
| | Physiological saline | 615 | 64 | 310 | 56 |
| Prescription A11 | Distilled water | 265 | 21 | 171 | 13 |
| | 5% glucose aqueous solution | 232 | 29 | 214 | 29 |
| | Physiological saline | 362 | 35 | 177 | 17 |

Note:
For each prescription, the redissolving time was the average of that of two bottles, and the insoluble particles were measured by combining two bottles, with measuring after 0 and 4 hours respectively.

From the phenomenon and results of the test, it can be seen that when the inclusion pH value was increased to 2.03, the inclusion difficulty increased (for example, it needs to be stirred at 40° C. for more than 1 hour), and the insoluble particles of the redissolving solution after lyophilization increased compared to those when inclusion pH=1.2. However, the situations of the insoluble particles of prescriptions A9-A11 all complied with the requirements for the preparation of intravenous injections.

2. Stability of Inclusion Samples with Different pH Values:

Lyophilized samples of prescriptions A9-A11 were taken to formulate two bottles of solutions (each with a concentration of 0.1 mg/mL) with water, respectively. The related substances were measured by HPLC (see the HPLC measurement conditions for the content and related substances described in Test Example 2). The results were shown as follows:

| Sample | Total impurity % | Main peak area | Average total impurity % |
|---|---|---|---|
| Time/minute | | 13.52 | |
| Prescription A9 | 0.74 | 80124726 | 0.79 |
| | 0.83 | 78985848 | |
| Prescription A10 | 0.73 | 81841754 | 0.76 |
| | 0.78 | 82415409 | |
| Prescription A11 | 0.77 | 82362183 | 0.81 |
| | 0.84 | 80282149 | |

It can be seen from the above table that the total impurities of prescriptions A10 and A11 are not significantly reduced compared to that of prescription A9. Considering that compared with the inclusion process with pH 1.2, the inclusion time is significantly increased and the inclusion process is more difficult when the inclusion pH is 2; therefore, the process is most preferably performed under condition of pH 1.2.

Example 6

Preparation and Evaluation of KX2-361.Benzene Sulfonate Lyophilized Agent and Redissolving Solution for Injection (the Concentration of HP-β-CD was 10%, and the Drug Loading was Low)

Prescriptions with the following composition were prepared:

| | HP-β-CD | API | Molar ratio (HP-β-CD:API) | Mass ratio (HP-β-CD:KX2-361) | Inclusion pH | Final pH value |
|---|---|---|---|---|---|---|
| Prescription A12 | 10% | 1 mg/mL | 31-39:1 | 100:0.72 | 1.2 | 4.0 |
| Prescription A13 | 10% | 0.7 mg/mL | 45-56:1 | 100:0.50 | 1.2 | 4.0 |

Note:
The molecular weight of HP-β-CD was 1431-1806. Therefore, the upper and lower limits of the molecular weight were respectively taken to calculate the molar ratio.

The above prescriptions according to the following steps successively:

1) 1.8 mL concentrated hydrochloric acid was placed in a 200 mL volumetric flask and diluted to 200 mL with distilled water to obtain a hydrochloric acid solution with a pH value of about 1.2.

2) HP-β-CD was weighed according to the above prescription amounts and added into two 25 mL volumetric flasks. The solution obtained in 1) was added respectively, and dissolved by ultrasound (ultrasonic frequency was 59 kHz) and diluted to about 25 mL with the above hydrochloric acid solution.

3) API was weighed according to the above prescription amounts and added to the above HP-β-CD solution respectively, and dissolved by ultrasound (ultrasonic frequency was 59 kHz).

4) The pH value of the solution obtained in 3) was adjusted to about 4.0 (±0.05) with 5N NaOH aqueous solution and 0.1N NaOH aqueous solution respectively. The solution was diluted to 50 mL with distilled water.

5) 0.1 g of activated carbon for injection was added to two solutions obtained in 4), stirred at room temperature for half an hour, and then filtered with a 0.45 μm polyether sulfone filter membrane and the prescription solutions were dispensed into 10 mL penicillin bottles (2 mL per bottle), and freeze dried.

The freeze-drying curve was as follows:

| Stage | Temperature (° C.) | Vacuum control (Pa) | Time (minute) | Vacuum pump state | Condenser pre-freezing (° C.) |
|---|---|---|---|---|---|
| 1 | −40 | OFF | 5 | OFF | −40 |
| 2 | −40 | OFF | 120 | OFF | |
| 3 | −40 | 20 ± 2 | 360 | ON | |
| 4 | −20 | 20 ± 2 | 360 | ON | |
| 5 | −20 | 10 ± 2 | 360 | ON | |
| 6 | 0 | 10 ± 2 | 360 | ON | |
| 7 | 0 | 10 ± 2 | 360 | ON | |
| 8 | 10 | No control | 360 | ON | |
| 9 | 10 | No control | 120 | ON | |

Sample state after freeze-drying: the samples had good formability. Lyophilized samples were white loose solids.

The lyophilized samples of the above two prescriptions (prescriptions A12 and A13) were redissolved, and their redissolving status and insoluble particles in physiological saline, distilled water and buffered saline solutions of different pH values (the formulation method was the same as that of the buffered saline solutions with pH 4, 5 and 6 in Example 3) were evaluated.

Redissolving method: 2 mL of the following redissolving medium was added to each penicillin bottle of each lyophilized sample, and then turned upside down 30 times, and if not dissolved, shaken until dissolved. Timing was after redissolving medium was added, and the redissolving test was repeated in each medium once.

The redissolving time of both prescriptions was about 1 minute.

Insoluble particles were shown as follows:

| Prescription | Redissolving medium | Insoluble particles (1 mL) | | | |
|---|---|---|---|---|---|
| | | 0 hour | | 4 hours | |
| | | ≥10 μm | ≥25 μm | ≥10 μm | ≥25 μm |
| Prescription A12 | Distilled water | 185.3 | 18.0 | 163.5 | 21.5 |
| | Physiological saline | 225.0 | 12.3 | 157.5 | 20.0 |
| | Medium with pH = 4 | 356.7 | 9.7 | 88.5 | 16.0 |
| | Medium with pH = 5 | 88.3 | 7.3 | 214.0 | 17.5 |
| | Medium with pH = 6 | 125.0 | 11.0 | 137.5 | 20.5 |
| Prescription A13 | Distilled water | 347.3 | 20.0 | 235.7 | 20.0 |
| | Physiological saline | 270.0 | 19.7 | 303.0 | 22.3 |
| | Medium with pH = 5 | 349.7 | 33.7 | 239.7 | 11.3 |

Note:
each value in the table was the average of three measurements.

From the above results, it can be found that both A12 and A13 meet the requirements of intravenous injections, and compared with prescription A13, the prescription A12 has less insoluble particles, but compared with prescription A9 (20% HP-β-CD+2 mg/mL API), prescription A12 has more insoluble particles. It shows that when the concentrations of hydroxypropyl-β-cyclodextrin and of the drug are reduced in equal proportion, the inclusion ability of low concentration cyclodextrin to encapsulate drug weakens. Therefore, it is also important for the development of KX2-361 injection to further select suitable concentration of hydroxypropyl-β-cyclodextrin and inclusion concentration of the drug based on the present disclosure.

Comparative Example 1

Drug Solubility Test

KX2-361 and its salts are all poorly soluble drugs, and the solubility of KX2-361.benzene sulfonate in the following media was tested comparatively in this comparative example.

(1) Aqueous Solution Containing Surfactant

The drug (KX2-361.benzene sulfonate) (containing 10 mg of KX2-361) was added to each of 10% Cremophor EL aqueous solution (50 ml), 2% Tween80 aqueous solution (50 ml), 8% Solutol HS15 aqueous solution (50 ml) and 0.6% Poloxamer 188 aqueous solution (50 ml), respectively, and the drug failed to completely dissolve after magnetic stirring for 1 hour.

(2) Single Solubilizer (Anhydrous)

The drug may be dissolved using a sufficient amount of solubilizer alone, but the solubility is generally very low; and the drug solution may not be unprecipitated during the dilution process with water. The content of each component of the system when drugs precipitate was shown in Table 4.

TABLE 4

Water-addition-precipitating critical point of drug solution of each solubilizer

| Solubilizers | KX2-361.benzene sulfonate | Water | Temperature |
|---|---|---|---|
| Cremophor EL 17.1 g | 100 mg | 6.7 g | 40° C. |
| Solutolo HS-15 10 g | 100 mg | 4.5 g | 40° C. |
| Solutolo HS-15 15 g | 100 mg | 8.7 g | 28° C. |
| Solutolo HS-15 20 g | 100 mg | 12.6 g | 28° C. |

(3) Single Non-Aqueous Solvent or Composite Solvent

In this study, a dissolution test was performed using a single non-aqueous solvent ethanol. It was found that the solubility of KX2-361.benzene sulfonate in ethanol was 1.12-2.38 mg/mL, that is, about 50-100 ml of ethanol was needed to dissolve 100 mg of the drug, apparently, a large amount of ethanol can not be used for intravenous administration.

In this study, a dissolution test was also performed using composite solvents composed of PEG400 or PEG200 and absolute ethanol, respectively. It was found that there was also a problem that the required solvent volume was too large and can not be diluted with aqueous solution system.

In addition, in this study, dissolution tests were also performed using a single non-aqueous solvent propylene glycol, or a composite solvent composed of propylene glycol and other non-aqueous solvent. It was found that the drug containing 50 mg of KX2-361 (KX2-361.benzene sulfonate) could substantially be dissolved using 20 ml of propylene glycol alone, but a trace of small particles was still present in the clear solution. When the non-aqueous solvent propylene glycol was used in combination with other solvents such as ethanol and PEG400, it did not contribute to the dissolution of the drug substantially.

(4) Composite Solvent Composed of Solubilizer and Other Solvents

The drug was solubilized with a binary or ternary system composed of a solubilizer (Cremophor EL or Solutolo HS 15) and a solvent (including water and propylene glycol), and two kinds of following solvent systems were selected to dissolve the drugs, namely: ① a solvent system of propylene glycol: Cremophor EL (50:50) (v/v) (5 ml), which can dissolve drug containing 50 mg KX2-361, and obtain a solution having good stability; ② 11.5 ml of a composite solvent (composed of 10 ml of propylene glycol, 1 ml of Cremophor EL and 0.5 ml of water), which also can dissolve the drug. Next, the dilution stability of these two solvent systems was tested.

(5) Dilution Stability Test

The dilution stability test was performed on the above drug-containing solution that can be dissolved clearly. Equal volume dilutions were performed using the aqueous solutions containing different surfactants described in (1), 0.9% sodium chloride injection or 5% glucose injection, and it was found that the solutions all become turbid, i.e., the drug was precipitated.

The above tests showed that in the current solvents, solubilizers, or mixed systems that can be used for injection, the drugs of the present disclosure cannot achieve high solubility or can not be diluted even after dissolution, that is, it is difficult to ensure that the drug solution would not precipitate after entering blood vessels.

Comparative Example 2

Measurement of Inclusion Ability of Different Concentrations and Kinds of Cyclodextrins for Encapsulating API Different kinds of cyclodextrins were dissolved with an aqueous hydrochloric acid solution (0.1N) having a pH value of 1.2 to determine the saturation concentration of each cyclodextrin. The KX2-361.benzene sulfonate was dissolved in different concentrations and kinds of cyclodextrin solutions to investigate the inclusion ability and inclusion effect of different concentrations and kinds of cyclodextrin for encapsulating API.

(1) A certain amount of α-, β- and γ-cyclodextrin were weighed and added into a 10 mL volumetric flask, then an aqueous hydrochloric acid solution of pH 1.2 was gradually added until reaching the scale of the flask, and the flask was shocked and ultrasound was performed to dissolve the cyclodextrin. The maximum amount of cyclodextrin capable of being dissolved in a 10 mL solution was recorded. The experimental results show that the maximum solubilities of α-cyclodextrin, β-cyclodextrin and γ-cyclodextrin in aqueous hydrochloric acid solution of a pH value of 1.2 are about 8%, about 1% and about 20%, respectively.

(2) 8% α-cyclodextrin solution, 1% β-cyclodextrin solution, 20% γ-cyclodextrin solution, 20%, 30%, and 40% sulfobutyl ether-β-cyclodextrin solution and 20%, 30%, and 40% hydroxypropyl-β-cyclodextrin solution were formulated with hydrochloric acid aqueous solution of a pH value of 1.2.

A certain amount of API was weighed and added into an appropriate volume of the cyclodextrin solution. If API was completely dissolved, the solution was filtered with a 0.45 μm PTFE filter membrane, and the pH value was slowly adjusted to 4.0 with a 5N NaOH aqueous solution and a 0.1N NaOH aqueous solution, observing during the pH adjusting procedure. If the solution became turbid when adjusting the pH value, try to reduce the concentration of API. The clear solution after the pH adjustment was left to stand to observe the state of the solution after standing for 2 hours, 4 hours, and 24 hours. The experimental process and results were shown in Table 5 below:

TABLE 5

Detection of inclusion ability of different kinds and concentrations of cyclodextrin for encapsulating API

| API concentration | Kinds and concentrations of cyclodextrin | Molar ratio (corresponding to cyclodextrin:API) | Solution phenomenon when the pH value was adjusted to 4 | Standing for 2 h Phenomenon | Standing for 4 h Phenomenon |
|---|---|---|---|---|---|
| 14 mg/ml | 40% HP-β-CD | 9-11:1 | The solution of pH 4.02 became light in color and clarified | Solution clarification | Solution clarification |
| | 40% SBE-β-CD | 12-13:1 | The solution of pH <4 became light in color and turbid | / | / |
| 10.6 mg/ml | 40% HP-β-CD | 12-15:1 | The solution of pH 4.02 became light in color and clarified | Solution clarification | Solution clarification |
| | 40% SBE-β-CD | 15-17:1 | The solution of pH <4 became light in color and turbid | / | / |
| 8.0 mg/ml | 30% HP-β-CD | 12-15:1 | The solution of pH 4.25 became light in color and clarified | Solution clarification | Solution clarification |
| | 30% SBE-β-CD | 15-17:1 | The solution of pH <4 became light in color and turbid | / | / |

TABLE 5-continued

Detection of inclusion ability of different kinds and concentrations of cyclodextrin for encapsulating API

| API concentration | Kinds and concentrations of cyclodextrin | Molar ratio (corresponding to cyclodextrin:API) | Solution phenomenon when the pH value was adjusted to 4 | Standing for 2 h Phenomenon | Standing for 4 h Phenomenon |
|---|---|---|---|---|---|
| 4.0 mg/ml | 30% HP-β-CD | 23-30:1 | The solution of pH 3.95 became light in color and clarified | Solution clarification | Solution clarification |
|  | 30% SBE-β-CD | 30-35:1 | The solution of pH 4.07 became light in color and turbid | White precipitate | / |
| 2.7 mg/ml | 20% HP-β-CD | 23-29:1 | The solution of pH 3.99 became light in color and clarified | Solution clarification | Solution clarification |
|  | 20% SBE-β-CD | 30-34:1 | The solution of pH 3.95 became light in color and turbid | White precipitation | / |
|  | 40% SBE-β-CD | 60-69:1 | The solution of pH 3.97 became light in color and clarified | Solution clarification | Solution clarification |
| 8 mg/ml | 8% α-CD | 6:1 | The solution of pH 1.21 became light in color and turbid | / | / |
| 4 mg/ml | 8% α-CD | 12:1 | The solution of pH 1.31 became light in color and turbid | / | / |
| 2 mg/ml | 8% α-CD | 23:1 | The solution of pH 1.49 became light in color and turbid | / | / |
| 1 mg/ml | 8% α-CD | 46:1 | The solution of pH 2.37 became light in color and turbid | / | / |
| 1 mg/ml | 1% β-CD | 5:1 | The solution of pH 1.18 became light in color and turbid | / | / |
| 0.5 mg/ml | 1% β-CD | 10:1 | The solution of pH 1.81 became light in color and turbid | / | / |
| 0.5 mg/ml | 20% γ-CD | 174:1 | turbid | / | / |

/: Observation was terminated

According to the experimental phenomena and results, the inclusion effect of HP-β-CD for encapsulating API was significantly better than that of SBE-β-CD, and the inclusion effects of α-cyclodextrin, β-cyclodextrin, and γ-cyclodextrin for encapsulating API were all poor.

Example 7

Preparation and Evaluation of Oral Tablets (I) Preparation of Lyophilized Powder Preparation of hydrochloric acid aqueous solution of pH 1.2: 0.9 ml of concentrated hydrochloric acid was added into a 100 ml volumetric flask and diluted to 100 ml with distilled water.

Preparation of 30% HP-β-CD solution and 7 mg/ml drug-containing solution (molar ratio of HP-β-CD: API was 13-17:1, mass ratio of HP-β-CD: KX2-361 was 100:1.68).

70 ml of hydrochloric acid aqueous solution of pH 1.2 was added to a 250 ml beaker. 30 g of HP-β-CD was weighed and added to the hydrochloric acid aqueous solution under magnetic stirring until all of HP-β-CD was dissolved.

700 mg of KX2-361.benzene sulfonate was weighed, API was added to the formulated HP-β-CD solution under magnetic stirring, the drug was dissolved completely by ultrasound (ultrasonic frequency was 59 kHz). The pH value of the drug solution was adjusted to about 4.0 with 5N NaOH aqueous solution and 0.1 N NaOH aqueous solution, and an appropriate amount of distilled water was added to dilute final volume to 100 ml, the final pH was measured as 4.0. Or dilute directly without adjusting pH (i.e., the pH of drug solution is 1.2).

Filtration: the drug solution was filtered through a 0.45 μm PES filter membrane and the filtrate was placed in a stainless steel tray, with a liquid level of about 0.3 cm.

Freeze-drying: freeze-drying curves was shown in the table

| Stage | Temperature (° C.) | Vacuum control (Pa) | Time (minute) | Vacuum pump state | Condenser pre-freezing (° C.) |
|---|---|---|---|---|---|
| 1 | −40 | OFF | 5 | OFF | −40 |
| 2 | −40 | OFF | 120 | OFF | — |
| 3 | −40 | 20 ± 2 | 360 | ON | — |
| 4 | −20 | 20 ± 2 | 360 | ON | — |
| 5 | −20 | 10 ± 2 | 360 | ON | — |
| 6 | 0 | 10 ± 2 | 360 | ON | — |
| 7 | 0 | 10 ± 2 | 360 | ON | — |
| 8 | 10 | No control | 360 | ON | — |
| 9 | 10 | No control | 60 | ON | — |

(B) Prescription Process and Tableting Process

Lyophilized powder (pH 1.2) and lyophilized powder (pH 4.0) were sieved through a 40 mesh sieve.

Raw materials were weighed and mixed according to the ratios provided by the prescriptions.

Tablet with 14 mg API per tablet using a 19×8 special-shaped punch. During the tableting process, the tablet thickness was adjusted according to the hardness and the hardness was controlled in a range of 50-100 N.

The dissolution characteristics of the tablets of which hardness and tablet weight were both qualified were investigated.

TABLE 5

| | Prescription designed (content of API was 14 mg) | | | |
|---|---|---|---|---|
| Prescription composition | Prescription B1 | Prescription B2 | Prescription B3 | Prescription B4 |
| pH 4.0 lyophilized powder (mg) | 614 | | | 614 |
| pH 1.2 lyophilized powder (mg) | | 614 | 614 | |
| Magnesium stearate (mg) | 3.07 (0.5% (w/w)) | 3.07 (0.5% (w/w)) | 6.14 (1% (w/w)) | 6.14 (1% (w/w)) |

(III) Evaluation of Dissolution

After the tableting scale increases, sticking and picking will occur in the tableting process of prescriptions B1 and B2 containing 0.5% magnesium stearate.

Dissolution Test Method:

Formulation of dissolution medium (pH 4.0, containing 1.0% SDS): 1.22 g of sodium acetate trihydrate and 10 g of SDS were dissolved in 950 ml of pure water, adjusted to pH 4.0 with acetic acid, and final volume was adjusted to 1 L.

The rotary basket method (the method refers to the First Method, Dissolution and Release Measurement Method, *Chinese Pharmacopoeia* Part IV 0903, 2015 Edition) was used in the test, 900 ml of dissolution medium was used for each tablet, rotation rate was 50 rpm, and temperature was 37° C. The sampling time points were 5, 10, 15, 20, 30, 45, 60 and 90 minutes, respectively. The rotation rate was adjusted to 250 rpm after 60 minutes, and samples at 90 minutes were taken as the ultimate dissolution of each tablet.

The dissolution amount of API was detected by HPLC (the process refers to HPLC measurement conditions of the content and the related substances described in Test Example 2), and then the dissolution was calculated with an external standard method.

According to the above method, the dissolution of the prescriptions B1, B3 and B4 was measured and compared, as shown in the following table:

TABLE 6

| | Dissolution results | | | | | |
|---|---|---|---|---|---|---|
| | Prescription B3 | | Prescription B4 | | Prescription B1 | |
| Time (minute) | Average, % | RSD | Average, % | RSD | Average, % | RSD |
| 0 | 0.0 | 0.0 | 0.0 | 0.0 | 0.0 | 0.0 |
| 5 | 37.9 | 7.2 | 39.1 | 0.8 | 41.2 | 5.9 |
| 10 | 70.9 | 6.1 | 73.2 | 4.0 | 78.1 | 2.6 |
| 15 | 95.4 | 3.6 | 97.8 | 3.8 | 96.7 | 0.2 |
| 20 | 103.2 | 0.4 | 100.8 | 1.4 | 98.2 | 0.6 |
| 30 | 103.2 | 0.6 | 101.2 | 1.3 | 98.3 | 0.9 |
| 45 | 103.3 | 0.6 | 101.3 | 1.2 | 98.4 | 0.7 |
| 60 | 102.9 | 0.7 | 100.9 | 1.3 | 98.3 | 0.1 |
| 90 | 103.1 | 0.4 | 101.2 | 1.2 | 98.2 | 0.8 |

The comparison between prescription B3 and B4 shows that, it will have little effect on the dissolution results whether the pH value of the drug solution is adjusted from 1.2 to 4.0 before lyophilization.

The comparison between prescription B1 and prescription B4 shows that, after increasing the magnesium stearate from 0.5% (w/w) to 1% (w/w), the API dissolution rate is slightly slower within 15 minutes, but all the API dissolution rates reach more than 95% at 15 minutes.

Comparative Example 3

Comparative Test of Bioavailability of Tablets

The prescription B4 tablet of Example 7 was orally administered to dogs, and test substance for intravenous administration was intravenously injected to dogs at a dose containing 0.5 mg/kg of KX2-361 for comparison, and then the absolute bioavailability of the oral tablet was calculated.

Operation Method:

1. Oral administration: Three healthy male beagle dogs (weight range was 8-12 kg, number of dogs is 201M\201M\203M, respectively) were taken and each dog was given a single oral dose of 5 tablets. The dogs were fasted overnight before administration and refed at 4 hours after administration; the dogs were prohibited drinking water for 1 hour before and 1 hour after administration.

2. Intravenous injection:

Preparation of test substances for intravenous administration: 19.34 mg of KX2-361.benzene sulfonate was accurately weighed and placed in a glass bottle, 5.565 mL of ethanol was added, whirled and then sonicated at 24° C. for 3 minutes, and 33.393 mL of PEG400 was added, whirled and then sonicated at 24° C. for 4 minutes, 16.696 mL of physiological saline was added, whirled and then sonicated at 24° C. for 4 minutes to obtain a colorless and transparent solution with theoretical concentration of 0.25 mg/mL.

The test dogs were fasted overnight before administration and fed four hours after the administration. The test substances was administered by a slow intravenous bolus (about 8 minutes), the dogs were prohibited drinking water for 1 hour before and 1 hour after administration.

3. Determination of bioavailability: for the oral administration group and the intravenous administration group, blood was sampled by puncturing the forelimb cephalic vein (about 0.5 mL) into anticoagulant tubes containing 5 uL EDTA-K2 (20%) 0.083 (only for the intravenous administration group), 0.25, 0.5, 1, 2, 4, 8 and 24 hours after administration. The blood samples were centrifuged at 8000 rpm for 6 minutes (placed on wet ice before centrifuging) within 1 hour. The supernatant, i.e., plasma, was taken, and cryostoraged at −20° C. in a refrigerator for LC-MS/MS analysis with mass spectrometer (tolbutamide was used as internal standard, mode: APCI ionization, MRM detection). The pharmacokinetic parameters are shown in the table below, and the curve of the plasma concentration over time is shown in FIG. 1. The area under the curve$_{(0-t)}$ (AUC$_{(0-t)}$) of the intravenous administration group was 164.3. The calculation formula of absolute bioavailability (F %) is: F %=(oral AUC$_{(0-t)}$/oral dose)/(intravenous AUC$_{(0-t)}$/intravenous dose)×100%.

TABLE 7

| | | Animal number | | | | |
|---|---|---|---|---|---|---|
| | Sampling time | 201M | 202M | 203M | Average | RSD |
| Plasma concentration (ng/mL) | 0.25 | 766.4 | 92.8 | 1045.2 | 634.8 | 489.6 |
| | 0.5 | 548.4 | 316.5 | 923.8 | 596.2 | 306.5 |
| | 1.00 | 155.1 | 494.1 | 565.3 | 404.8 | 219.2 |
| | 2.00 | 47.8 | 196.1 | 220.1 | 154.7 | 93.3 |
| | 4.00 | 12.1 | 46.5 | 83.9 | 47.5 | 35.9 |
| | 8.00 | 1.4 | 5.6 | 8.3 | 5.1 | 3.5 |
| | 24.00 | BLQ | BLQ | 0.5 | 0.5 | NA |
| Weight of dog | kg | 11.68 | 11.96 | 11.17 | 11.60 | 0.40 |
| Dose | mg/kg | 4.37 | 4.26 | 4.57 | 4.40 | 0.15 |
| Area under the curve$_{(0-t)}$ | ng/mL*h | 624.4 | 957.3 | 1700.6 | 1094.1 | 551.0 |
| Area under the curve$_{(0-\infty)}$ | ng/mL*h | 626.7 | 967.6 | 1700.6 | 1098.3 | 548.7 |
| Average residence time$_{(0-t)}$ | h | 0.93 | 1.75 | 1.82 | 1.50 | 0.50 |
| Corrected distribution volume | L/kg | 11.99 | 8.19 | 4.47 | 8.22 | 3.76 |
| Corrected clearance | L/h/kg | 6.97 | 4.40 | 2.69 | 4.69 | 2.16 |
| Half life | h | 1.19 | 1.29 | 1.15 | 1.21 | 0.07 |
| Time to peak | h | 0.25 | 1.00 | 0.25 | 0.50 | 0.43 |
| Peak concentration | ng/mL | 766.4 | 494.1 | 1045.2 | 768.6 | 275.6 |
| Bioavailability | % | 43.5 | 68.3 | 113.3 | 75.7 | 35.4 |

It can be seen that, relatively high bioavailability (average F % was 75.7%) is achieved by orally administering the tablets to dogs.

Other preparation schemes such as preparations 1 and 2 (formulation and process are shown below) were used to detect the absorption of the animal in vivo. Orally administrate to dogs, research pharmacodynamics (the method is the same as the above), and calculate the absolute bioavailability, and the results are as follows:

| Preparation | Formulation (Mass ratio) | Brief Description of Process | Absolute bioavailability F (%) of Beagle dog |
|---|---|---|---|
| Preparation 1 | KX2-361•BSA:caprylocaproyl macrogolglycerides:polyglyceryl oleate:1,2-propanediol (0.3:22.5:3.75:3.75) | The caprylocaproyl macrogolglycerides, polyglycerol oleate, and propanediol were mixed uniformly in proportion; the drug was dissolved with the mixed liquid; the drug solution was encapsulated. | 3.24% |
| Preparation 2 | KX2-361•BSA:povidone K30:sodium lauryl sulfate:micro powder silica gel:talcum powder:tartaric acid core = 22.5:5.25:1:12.5:75:150 | An appropriate amount of water was added as a dispersant to povidone K30, and drug and sodium lauryl sulfate were added for wet grinding; micro powder silica gel and talcum powder were added to the suspension, and the suspension was applied to tartaric acid core in a fluidized bed, dried and filled into capsules. | 3.86% |
| Prescription B4 | See Example 7 | See Example 7 | 75.7% |

It can be seen that, compared with the other two preparation schemes, KX2-361.benzene sulfonate and hydroxypropyl-β-cyclodextrin were made as an inclusion complex, followed by tableting, achieving higher absorption (about 20 times), which shows that, in the preparations of the present disclosure, the adjuvant hydroxypropyl-β-cyclodextrin has a significant effect in enhancing the in vivo bioavailability of drug.

Test Example 6

Stability Investigation

Tablets of prescription B3 (containing lyophilized powder of pH 1.2) and prescription B4 (containing lyophilized powder of pH 4.0) were loaded into high-density polyethylene (HDPE) bottles with desiccant (allochroic silica gel), then placed in a stability box at 40° C./75% RH for high-temperature acceleration test, samples were taken at the end of 1 month, 2 months, and 3 months respectively to measure the related substances (the method refers to HPLC measurement conditions of the content and the related substances described in Test Example 2).

TABLE 8

Tablet Stability Investigation Results of Prescription B3 and B4

| Number | Sample | Total impurity (%) |
|---|---|---|
| 1 | Prescription B3-0 day | 0.36 (n = 2) |
| 2 | Prescription B 3-1 month | 2.28 |
| 3 | Prescription B 3-2 months | 3.88 |

TABLE 8-continued

Tablet Stability Investigation Results of Prescription B3 and B4

| Number | Sample | Total impurity (%) |
|---|---|---|
| 4 | Prescription B 3-3 months | 9.04 |
| 5 | Prescription B4-0 day | 0.30 (n = 2) |
| 6 | Prescription B4-1 month | 0.39 |

TABLE 8-continued

Tablet Stability Investigation Results of Prescription B3 and B4

| Number | Sample | Total impurity (%) |
|---|---|---|
| 7 | Prescription B4-2 months | 0.26 |
| 8 | Prescription B4-3 months | 0.65 |

Note:
n = 2 represents that two samples are taken and measured respectively, and the result is the average of the two samples.

In the investigation process of acceleration for 1 month to 3 months, impurities of prescription B3 increased, which may be in association with the strong acid environment; impurities of prescription B4 increased slightly but showed no remarkable change. It can be seen that the process that pH is adjusted back after inclusion is preferable for the preparation of oral tablets.

Example 8

Preparation and Evaluation of Tablets (I) Lyophilization Process

Formulation of hydrochloric acid aqueous solution of pH 1.2:9 ml concentrated hydrochloric acid was added into a 1000 ml volumetric flask and diluted to the final volume with distilled water.

Formulation method of 30% HP-β-CD solution: 700 ml of hydrochloric acid aqueous solution of pH 1.2 was added into a 1000 ml beaker. 300 g of HP-β-CD was weighed and added into the hydrochloric acid aqueous solution of pH 1.2 under magnetic stirring until all the HP-β-CD was dissolved, distilled water was added to bring the volume to 1000ml. Formulate a certain amount for use.

(1) Formulation of about 7 mg/ml drug-containing preparation (molar ratio of HP-β-CD: API was 13-17:1, and mass ratio of HP-β-CD: KX2-361 was 100:1.68): 1750 mg of KX2-361.benzene sulfonate was weighed and then added to 250 ml of the above HP-β-CD solution under stirring, dissolved completely by ultrasound (ultrasonic frequency was 59 kHz), and pH value was adjusted to 4.0 with 5N NaOH aqueous solution and 0.1N NaOH aqueous solution. Then the solution was filtered through a 0.45 μm PES filter membrane and the filtrate was placed in a stainless steel tray, with a liquid level of about 0.5 cm. The filtrate was lyophilizated and then named as lyophilized powder I (lyophilization method was the same as Example 7, the same below).

(2) Formulation of about 14 mg/ml of drug-containing preparation (molar ratio of HP-β-CD: API was 7-8:1, mass ratio of HP-β-CD: KX2-361 was 100:3.36): 4200 mg of KX2-361.benzene sulfonate was weighed and then added to 300 ml of the above HP-β-CD solution under stirring, dissolved completely by ultrasound (ultrasonic frequency was 59 kHz). The solution was filtered through a 0.45 μm PES filter membrane and the filtrate was placed in a stainless steel tray, with a liquid level of about 0.5 cm. The filtrate was lyophilizated and then named as lyophilized powder II.

(3) Formulation of 21 mg/ml of drug-containing preparation (molar ratio of HP-β-CD: API was 4-6:1, mass ratio of HP-β-CD: KX2-361 was 100:5.03): 6300 mg of KX2-361.benzene sulfonate was weighed and then added to 300 ml of the above HP-β-CD solution under stirring, and the API was not completely dissolved by ultrasound (ultrasonic frequency was 59 kHz) for 30 minutes and a certain amount of insoluble particles were still present. The solution was filtered through a 0.45 μm PES filter membrane and the filtrate was placed in a stainless steel tray, with a liquid level of about 0.5 cm. After the 21 mg/ml of the drug-containing preparation was filtered, the concentration was 20.66 mg/ml calibrated with HPLC. The filtrate was lyophilizated and then named as lyophilized powder III.

(II) Prescription Composition and Tableting Process

The lyophilized powders prepared were sieved through a 40 mesh sieve respectively.

Raw materials were weighed according to the ratios designed by the following prescriptions.

| Prescription composition | Prescription B4 (prepared anew, API content is 14 mg) | Prescription B5 (API content is 28 mg) | Prescription B6 (API content is 42 mg) |
| --- | --- | --- | --- |
| Lyophilized powder I (mg) | 614 | | |
| Lyophilized powder II (mg) | | 628 | |
| Lyophilized powder III (mg) | | | 642 |
| Magnesium stearate (mg) | 6.14 (1%) | 6.28 (1%) | 6.42 (1%) |

Tablet with 600 mg HP-β-CD per tablet using a 19×8 special-shaped punch. During the tableting process, the tablet thickness was adjusted according to the hardness which was controlled in the range of 50-100 N.

According to the method described in Example 7, the dissolution characteristics of the tablets which have qualified hardness and tablet weight were investigated, see Table 9.

TABLE 9

Investigation results of dissolution (n = 3)

| Time (minute) | Prescription B4 | | Prescription B5 | | Prescription B6 | |
| --- | --- | --- | --- | --- | --- | --- |
| | Average, % | RSD | Average, % | RSD | Average, % | RSD |
| 0 | 0.0 | 0.0 | 0.0 | 0.0 | 0.0 | 0.0 |
| 5 | 39.1 | 0.8 | 33.6 | 3.6 | 29.6 | 11.4 |
| 10 | 73.2 | 4.0 | 60.6 | 1.9 | 57.3 | 6.1 |
| 15 | 97.8 | 3.8 | 82.6 | 2.4 | 81.1 | 4.4 |
| 20 | 100.8 | 1.4 | 95.4 | 1.7 | 95.4 | 2.7 |
| 30 | 101.2 | 1.3 | 97.1 | 1.7 | 98.8 | 0.6 |
| 45 | 101.3 | 1.2 | 97.2 | 2.1 | 99.3 | 0.4 |
| 60 | 100.9 | 1.3 | 97.5 | 2.2 | 99.3 | 0.2 |

Note:
n = 3 represents that three samples were taken and measured respectively, and the result was the average of the three samples.

Results of dissolution measurement are as follows:

Each prescription can dissolve over 95% in 20 minutes.

After the API content increased, the dissolution rate decreased, and the difference of dissolution rate between prescription B5 and prescription B6 was small, but both were slower than prescription B4.

Test Example 7

Study on Dissolution Effects of Dissolution Media Containing Different Concentrations of SDS on High-Dose Tablets In order to make the dissolution medium be more able to show its ability to distinguish prescriptions, the dissolution behaviors of the following prescriptions in dissolution media with different SDS concentrations were investigated.

The dissolution of the prescription B3 of Example 7 and the prescriptions B5 and B6 of Example 8 in dissolution media containing 0.5% SDS, 0.2% SDS, and no SDS was investigated. Data is shown in Tables 10-12.

Dissolution test method: rotary basket method, dissolution medium was 900 ml, rotation rate was 50 rpm, and temperature was 37° C. The sampling time points were 5, 10, 15, 20, 30, 45 and 60 minutes, respectively. The formulation method of the dissolution medium of pH 4.0 was the same as that described in Example 7. The difference is that, buffered saline solutions of pH 4.0 containing 5 g, 2 g, and 0 g SDS were used as 1 L dissolution media containing 0.5% SDS, 0.2% SDS, and no SDS, respectively.

TABLE 10

Dissolution of the three prescriptions in dissolution medium of pH 4.0 containing no SDS

| Time (minute) | Prescription B3 | | Prescription B5 | | Prescription B6 | |
| --- | --- | --- | --- | --- | --- | --- |
| | Average, % | RSD | Average, % | RSD | Average, % | RSD |
| 0 | 0.0 | 0.0 | 0.0 | 0.0 | 0.0 | 0.0 |
| 5 | 34.0 | 5.4 | 26.0 | 14.7 | 18.6 | 7.6 |
| 10 | 61.8 | 3.4 | 22.9 | 28.4 | 12.8 | 3.6 |
| 15 | 56.8 | 8.2 | 40.6 | 49.7 | 8.3 | 5.5 |
| 20 | 58.2 | 28.6 | 19.9 | 29.8 | 7.3 | 1.2 |
| 30 | 42.8 | 23.4 | 18.7 | 16.6 | 6.7 | 2.1 |
| 45 | 37.3 | 30.2 | 14.2 | 32.5 | 6.2 | 0.2 |
| 60 | 34.1 | 20.0 | 16.5 | 41.2 | 5.9 | 5.0 |
| 90 | 45.2 | 73.9 | 14.0 | 13.0 | 5.0 | 2.5 |

TABLE 11

Dissolution of the three prescriptions in dissolution medium of pH 4.0 containing 0.5% SDS

| Time (minute) | Prescription B3 | | Prescription B5 | | Prescription B6 | |
|---|---|---|---|---|---|---|
| | Average, % | RSD | Average, % | RSD | Average, % | RSD |
| 0 | 0.0 | 0.0 | 0.0 | 0.0 | 0.0 | 0.0 |
| 5 | 35.8 | 1.5 | 35.3 | 4.6 | 32.6 | 0.2 |
| 10 | 71.4 | 0.6 | 61.2 | 0.3 | 60.8 | 2.3 |
| 15 | 91.3 | 4.8 | 85.6 | 0.9 | 83.6 | 1.4 |
| 20 | 99.5 | 0.7 | 95.4 | 0.6 | 94.9 | 2.0 |
| 30 | 99.6 | 0.4 | 96.9 | 0.1 | 97.3 | 1.5 |
| 45 | 99.7 | 0.2 | 97.5 | 0.1 | 97.9 | 1.1 |
| 60 | 99.6 | 0.1 | 97.6 | 0.4 | 98.1 | 1.3 |
| 90 | 99.7 | 0.3 | 97.7 | 0.0 | 98.0 | 1.1 |

TABLE 12

Dissolution of the three prescriptions in dissolution medium of pH 4.0 containing 0.2% SDS

| Time (minute) | Prescription B3 | | Prescription B5 | | Prescription B6 | |
|---|---|---|---|---|---|---|
| | Average, % | RSD | Average, % | RSD | Average, % | RSD |
| 0 | 0.0 | 0.0 | 0.0 | 0.0 | 0.0 | 0.0 |
| 5 | 34.1 | 10.8 | 32.1 | 2.8 | 26.9 | 3.1 |
| 10 | 64.0 | 6.5 | 57.8 | 3.7 | 51.2 | 2.2 |
| 15 | 89.2 | 4.7 | 78.4 | 0.2 | 69.8 | 5.4 |
| 20 | 96.3 | 0.1 | 88.5 | 1.2 | 81.6 | 3.9 |
| 30 | 97.3 | 0.4 | 91.4 | 0.6 | 85.4 | 6.5 |
| 45 | 98.3 | 0.1 | 92.7 | 1.6 | 88.7 | 5.9 |
| 60 | 97.9 | 0.1 | 93.6 | 0.9 | 92.4 | 1.7 |
| 90 | 98.5 | 0.3 | 94.6 | 0.1 | 91.2 | 5.4 |

The observed phenomenon was that in the absence of SDS in the dissolution medium, a few floccules appeared in the dissolution cup of prescription B5, and a lot of floccules appeared in the dissolution cup of prescription B6. When 0.2% SDS or 0.5% SDS was contained in the dissolution medium, floccules appeared in the dissolution cup of prescription B6, and the floccules decreased after 30 minutes.

Conclusion: in the absence of SDS, the dissolution of the sample was greatly affected, and the dissolution of the three prescriptions was poor. Compared with the dissolution medium containing 0.5% SDS, when 0.2% SDS was contained, the dissolution rate of prescription B3 was similar to that in the dissolution medium containing 0.5% SDS, but the dissolution rate of prescriptions B5 and B6 slowed down and the ultimate dissolution decreased, which shows that the dissolution medium containing 0.2% SDS is not applicable to the dissolution of these two prescriptions. When the dissolution medium contained 0.5% SDS, dissolution of the three prescriptions was good and very similar to that when 1% SDS was contained, and the dissolution characteristics of the prescriptions B5 and B6 were not significantly different.

Example 9

Preparation and Evaluation of Tablets

Preparation of tablets of the prescription B16: 14 mg/ml of the drug was encapsulated by 40% HP-β-CD, and the preparation process of lyophilized powder was the same as that in Example 7 (adjusting the pH value back to 4.0). The lyophilized powder was sieved through a 40 mesh sieve, and lyophilized powder and magnesium stearate (magnesium stearate was in an amount of 1.0% (w/w) of lyophilized powder) were weighed and mixed uniformly; a 19×8 special-shaped punch was used for tableting, the weight of tablet was about 600 mg, hardness was 50-100N. The disintegration time was 8 minutes. The dissolution results are as follows:

TABLE 15

Comparison of dissolution results of prescription B16 and prescription B3

| Time (minute) | Prescription B3 | | Prescription B16 | |
|---|---|---|---|---|
| | Average, % | RSD | Average, % | RSD |
| 0 | 0.0 | 0.0 | 0.0 | 0.0 |
| 5 | 35.8 | 1.5 | 39.5 | 7.4 |
| 10 | 71.4 | 0.6 | 70.9 | 3.8 |
| 15 | 91.3 | 4.8 | 88.3 | 3.5 |
| 20 | 99.5 | 0.7 | 92.7 | 4.4 |
| 30 | 99.6 | 0.4 | 96.7 | 2.3 |
| 45 | 99.7 | 0.2 | 99.7 | 0.7 |
| 60 | 99.6 | 0.1 | 100.6 | 0.3 |
| 90 | 99.7 | 0.3 | 101.6 | 0.5 |

Conclusion: The dissolution of prescription B16 was slightly slower than that of prescription B3, but it dissolved over 85% at 15 minutes. The drug loading of each tablet (API content of each tablet) for prescription B16 was about 20.29 mg, which was about 45% higher than that of prescription B3, achieving the purpose of increasing drug loading.

Example 10

Preparation and Evaluation of Tablets

It can be seen from Test Example 6 that the stability of the tablet containing lyophilized powder of pH 1.2 was poor, and the stability of the tablet containing lyophilized powder of pH 4.0 was significantly improved. Therefore, try to adjust pH to 6.0 to ensure its stability.

(I) Lyophilization Process

1. Formulation of hydrochloric acid aqueous solution of pH 1.2: 0.9 ml concentrated hydrochloric acid was added into a 100 ml volumetric flask and diluted to 100 ml with distilled water.

2. Formulation of 40% HP-β-CD solution: 10 g of HP-β-CD was weighed and dissolved with an appropriate amount of hydrochloric acid aqueous solution of pH 1.2, and then transferred to a 25 ml volumetric flask, and diluted to the final volume with the above hydrochloric acid aqueous solution.

3. Formulation of about 14 mg/ml of drug-containing preparation: 56 mg of KX2-361.benzene sulfonate was weighed and then added to 4 ml of the above HP-β-CD solution. The drug was dissolved completely by ultrasound (ultrasonic frequency was 59 kHz).

4. pH adjustment: the pH value of the drug solution was adjusted to about 6.0 with 5N NaOH aqueous solution and 0.1 N NaOH aqueous solution. At this time, the solution was nearly colorless. No obvious turbidity and precipitation were observed after standing for 30 minutes. A few precipitation appeared after standing overnight and the liquid portion was a solution.

5. Preparation of lyophilized powder: after the pH value was adjust to about 6.0, the solution was filtered through a 0.22 am PES filter membrane and lyophilized. White lyophilized powder was obtained. The lyophilization process was the same as that in Example 7.

Investigation of redissolution: the lyophilized powder was redissolved with water, completed in about 10 minutes by shaking gently, with no apparent abnormality.

(II) Prescription Composition and Tableting Process

1. Lyophilized powder and each filler were sieved through a 40 mesh sieve respectively.

2. API and each filler were weighed according to the prescription design amount (see Table 16 and Table 17), and mixed, then mixed with the lubricant magnesium stearate by adding equal amount, and then mixed by sieving through 40 mesh sieve three times.

3. A Φ8 mm stamping die was used to tablet with tablet weight of about 200 mg (containing about 2 mg API). During the tableting process, the tablet thickness was adjusted according to the hardness which was controlled in the range of 50-100 N.

Experimental results: Tablets of each prescription were obtained successfully.

TABLE 16

| Prescription design 1 | | | | |
|---|---|---|---|---|
| | Prescription | | | |
| | Prescription B7 | Prescription B8 | Prescription B9 | Prescription B10 |
| Lyophilized powder (mg) | 60 | 60 | 60 | 60 |
| MCC pH 200 (mg) | 138 | 69 | | |
| Spray-dried lactose (mg) | | 69 | 138 | |
| Mannitol SD200 (mg) | | | | 138 |
| Magnesium stearate (mg) | 2 (1%) | 2 (1%) | 2 (1%) | 2 (1%) |

TABLE 17

| Prescription design 2 | | | | | |
|---|---|---|---|---|---|
| | Prescription | | | | |
| | Prescription B11 | Prescription B12 | Prescription B13 | Prescription B14 | Prescription B15 |
| Lyophilized powder (mg) | 60 | 60 | 60 | 60 | 60 |
| Spray-dried lactose (mg) | 128 | 128 | 134 | | 128 |
| Mannitol SD200 (mg) | | | | 134 | |
| PVPP XL (mg) | 10 | | | | |
| CC-Na (mg) | | 10 | | | 6 |
| Magnesium stearate (mg) | 2 (1%) | 2 (1%) | 6 (3%) | 6 (3%) | 6 (3%) |

A disintegration time limit tester was used to detect the disintegration time of each prescription tablet described above (method refers to the disintegration time test method, Appendix 0921, *Chinese Pharmacopoeia* Part IV, 2015 Edition) and the dissolution. Results are shown in Table 18 and Table 19.

TABLE 18

| Disintegration time results of each prescription tablet | | | | | | | | | |
|---|---|---|---|---|---|---|---|---|---|
| Prescription | B7 | B8 | B9 | B10 | B11 | B12 | B13 | B14 | B15 |
| Disintegration time (minute) | ~0.5 | ~1 | ~11 | ~6 | ~4 | ~4 | ~14 | ~6 | ~8 |

It can be seen from the results that the disintegration time of tablets of prescription B9 and prescription B13 was more than 10 minutes, while the disintegration time of other prescriptions was shorter, which was more conducive to the rapid dissolution of drug.

TABLE 19

| Investigation results of dissolution of each prescription tablet | | | | | | | | |
|---|---|---|---|---|---|---|---|---|
| | Prescription B7 | | Prescription B8 | | Prescription B9 | | Prescription B10 | |
| Time (minute) | Average, % | RSD | Average, % | RSD | Average, % | RSD | Average, % | RSD |
| 5 | 72.2 | 2.2 | 90.3 | 4.3 | 29.0 | 24.5 | 39.2 | 12.5 |
| 10 | 84.2 | 2.6 | 99.4 | 2.1 | 47.8 | 17.5 | 68.1 | 11.9 |

TABLE 19-continued

Investigation results of dissolution of each prescription tablet

| 15 | 91.2 | 2.1 | 101.9 | 1.9 | 65.4 | 19.2 | 85.3 | 8.9 |
| 20 | 95.0 | 1.2 | 101.4 | 0.8 | 78.6 | 19.5 | 92.0 | 7.6 |
| 30 | 97.0 | 0.9 | 100.8 | 1.0 | 95.9 | 8.0 | 92.4 | 7.2 |
| 45 | 98.2 | 0.7 | 101.0 | 1.0 | 98.8 | 4.9 | 93.1 | 6.8 |
| 60 | 98.5 | 0.7 | 101.6 | 0.8 | 98.2 | 5.3 | 92.5 | 7.2 |
| 90 (200 RPM) | 99.2 | 1.4 | 102.2 | 1.4 | 98.3 | 5.3 | 92.3 | 7.3 |

| | Prescription B12 | | Prescription B13 | | Prescription B14 | | Prescription B15 | |
|---|---|---|---|---|---|---|---|---|
| Time (minute) | Average, % | RSD | Average, % | RSD | Average, % | RSD | Average, % | RSD |
| 5 | 42.5 | 6.5 | 6.5 | 0.9 | 8.8 | 16.6 | 21.8 | 14.7 |
| 10 | 76.1 | 3.8 | 13.0 | 6.0 | 19.7 | 31.7 | 41.9 | 14.8 |
| 15 | 97.3 | 0.3 | 19.1 | 15.1 | 32.7 | 19.0 | 58.8 | 11.6 |
| 20 | 102.3 | 1.8 | 26.4 | 17.2 | 43.4 | 13.7 | 71.2 | 13.2 |
| 30 | 102.8 | 2.0 | 39.1 | 10.5 | 72.3 | 11.6 | 87.0 | 11.3 |
| 45 | 102.9 | 2.2 | 59.7 | 1.4 | 97.4 | 1.9 | 95.0 | 9.1 |
| 60 | 103.3 | 2.2 | 76.2 | 5.4 | 99.4 | 0.2 | 99.5 | 8.4 |
| 90 (200 RPM) | 102.6 | 2.1 | 103.8 | 1.3 | 99.6 | 0.4 | 104.2 | 2.3 |

From the dissolution data, it can be seen that the dissolution rates of prescriptions B9, B10, B13, B14, and B15 were all slow. The dissolutions of other prescriptions were more than 90% at 15 minutes, which showed the rapid dissolution ability of the drug from immediate release tablets.

The tablets of each prescription were placed under conditions such as high temperature (60° C.), high humidity (92.5% RH), −20° C., and was sampled and detected at a specific time point (method refers to HPLC measurement conditions of the content and the related substances described in Test Example 2), and compared with impurity increase of API. Results are shown in Table 20.

TABLE 20

Investigation results of stability of each prescription tablet

| | API | | | | | Prescription B11 | | |
|---|---|---|---|---|---|---|---|---|
| | 0 day | High temperature, 10 days | High temperature, 20 days | High humidity, 20 days | −20° C., 20 days | −20° C., 30 days | 50° C. 30 days | High humidity 30 days |
| Total impurity (%) | 0.33 | 0.32 | 0.32 | 0.31 | 0.36 | 1.18 | 2.34 | 0.75 |

| | Prescription B7 | | | | | | |
|---|---|---|---|---|---|---|---|
| | 0 day | High temperature, 10 days | High temperature 20 days | High humidity 10 days | High humidity 20 days | −20° C., 10 days | −20° C., 20 days |
| Total impurity (%) | 0.43 | 0.50 | 0.54 | 0.45 | 0.54 | 0.55 | 0.53 |

| | Prescription B8 | | | | | | |
|---|---|---|---|---|---|---|---|
| | 0 day | High temperature, 10 days | High temperature 20 days | High humidity 10 days | High humidity 20 days | −20° C., 10 days | −20° C., 20 days |
| Total impurity (%) | 0.40 | 0.46 | 0.45 | 0.51 | 0.54 | 0.57 | 0.47 |

TABLE 20-continued

Investigation results of stability of each prescription tablet

Prescription B12

| | 0 day | High temperature, 10 days | High temperature 20 days | High humidity 10 days | High humidity 20 days | −20° C., 10 days | −20° C., 20 days |
|---|---|---|---|---|---|---|---|
| Total impurity (%) | 0.42 | 0.43 | 0.45 | 0.40 | 0.50 | 0.45 | 0.42 |

Prescription B13

| | 0 day | High temperature, 10 days | High temperature 20 days | High humidity 10 days | High humidity 20 days | −20° C., 10 days | −20° C., 20 days |
|---|---|---|---|---|---|---|---|
| Total impurity (%) | 0.44 | 0.46 | 0.45 | 0.46 | 0.42 | 0.43 | 0.40 |

Prescription B14

| | 0 day | High temperature, 10 days | High temperature 20 days | High humidity 10 days | High humidity 20 days | −20° C., 10 days | −20° C., 20 days |
|---|---|---|---|---|---|---|---|
| Total impurity (%) | 0.42 | 0.46 | 0.45 | 0.49 | 0.43 | 0.42 | 0.40 |

Prescription B15

| | 0 day | High temperature, 10 days | High temperature 20 days | High humidity 10 days | High humidity 20 days | −20° C., 10 days | −20° C., 20 days |
|---|---|---|---|---|---|---|---|
| Total impurity (%) | 0.44 | 0.47 | 0.45 | 0.51 | 0.54 | 0.44 | 0.34 |

From the above table, it can be seen that the stability of prescription B11 was poor than other prescriptions, and the stabilities of prescriptions B7 and B8 were also undesirable. No abnormalities were observed in the remaining prescription tablets after standing for 20 d (days) under each condition. In summary, dissolution data shows that prescription B12 is a preferable prescription.

The invention claimed is:

1. A method of preparing an oral preparation for treatment of cell proliferative diseases which comprises hydroxypropyl-β-cyclodextrin and an active ingredient that is KX2-361 represented by the following Formula 1 or a medicinal salt thereof:

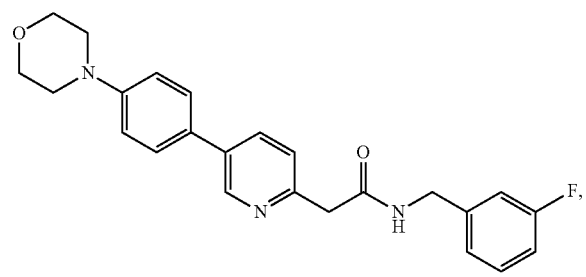

Formula 1 comprising the following steps:
A) providing a first solution in which hydroxypropyl-β-cyclodextrin is dissolved, the first solution has a pH value of 1-2;
B) mixing KX2-361 or a medicinal salt thereof with the first solution to prepare a second solution in which the KX2-361 or the medicinal salt thereof is dissolved; and
C) drying the second solution to obtain a dried product.

2. The method of claim 1, wherein in the first solution, the hydroxypropyl-β-cyclodextrin has a concentration of 10% (w/v)~50% (w/v).

3. The method of claim 1, wherein in the second solution, the KX2-361 or the medicinal salt thereof has a concentration of 0.5 mg/ml to 15 mg/ml, measured by KX2-361.

4. The method of claim 1, wherein in the second solution, a molar ratio of the KX2-361 or the medicinal salt thereof to the hydroxypropyl-β-cyclodextrin is 1: (4-59).

5. The method of claim 1, further comprising I) adjusting the pH value of the second solution to 3-7 before the step C) and after the step B).

6. The method of claim 1, further comprising D) tableting the dried product after the step C).

7. The method of claim 6, wherein the step D) includes mixing the dried product with one or more excipients selected from the group consisting of a filler, a disintegrant and a lubricant, then performing the tableting.

8. The method of claim 7, wherein the filler is one or more selected from the group consisting of a microcrystalline, a cellulose, a lactose, a starch and a mannitol.

9. The method of claim 7, wherein the disintegrant is one or more selected from the group consisting of croscarmellose sodium, cross-linked povidone and sodium carboxymethyl starch.

10. The method of claim 7, wherein the lubricant is one or more selected from the group consisting of a magnesium stearate, a micro powder silica gel and a talcum powder, and the content of the lubricant is 0.5% (w/w)~3% (w/w) based on the total weight of the oral preparation.

11. The method of claim 1, wherein the medicinal salt of KX2-361 is KX2-361.monophenyl sulfonate, KX2-361.dihydrochloride, KX2-361.monophosphate and/or KX2-361.diphosphonate.

12. An oral preparation prepared by the method of claim 1.

13. The oral preparation of claim 12, wherein molar ratio of the active ingredient to the hydroxypropyl-β-cyclodextrin is 1:(459).

14. The oral preparation of claim 12, wherein the active ingredient is KX2-361, KX2-361.monophenyl sulfonate, KX2-361.dihydrochloride, KX2-361.monophosphate and/or KX2-361.diphosphonate.

15. The oral preparation of claim 12, wherein at least a part of the active ingredient is encapsulated by at least a part of the hydroxypropyl-β-cyclodextrin to form a drug inclusion complex.

16. The oral preparation of claim 12, further comprising a medicinal excipient.

17. The oral preparation of claim 16, wherein the medicinal excipient is one or more selected from the group consisting of a filler, a disintegrant and a lubricant.

18. The oral preparation of claim 17, wherein the filler is one or more selected from the group consisting of a microcrystalline cellulose, a lactose, a starch and a mannitol.

19. The oral preparation of claim 17, wherein the disintegrant is one or more selected from the group consisting of croscarmellose sodium, cross-linked povidone and sodium carboxymethyl starch.

20. The oral preparation of claim 17, wherein the lubricant is one or more selected from the group consisting of magnesium stearate, micro powder silica gel and talcum powder, and the content of the lubricant is 0.5% (w/w)~3% (w/w) based on the total weight of the oral preparation.

21. The oral preparation of claim 12, wherein the oral preparation is in the form of a tablet, wherein the content of the active ingredient in a single dose of tablet is 0.5% (w/w)~6.5% (w/w).

* * * * *